United States Patent
Frumkin et al.

(10) Patent No.: US 12,152,273 B2
(45) Date of Patent: *Nov. 26, 2024

(54) METHODS AND SYSTEMS FOR DETECTING METHYLATION CHANGES IN DNA SAMPLES

(71) Applicant: NUCLEIX LTD., Rehovot (IL)

(72) Inventors: Danny Frumkin, Rehovot (IL); Adam Wasserstrom, Ness Ziona (IL); Revital Knirsh, Rosh Haayin (IL); Orna Savin, Herzliya (IL)

(73) Assignee: NUCLEIX LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/902,979

(22) Filed: Sep. 5, 2022

(65) Prior Publication Data

US 2023/0220458 A1     Jul. 13, 2023

Related U.S. Application Data

(62) Division of application No. 17/439,906, filed as application No. PCT/IL2020/050314 on Mar. 17, 2020, now Pat. No. 11,434,528.

(60) Provisional application No. 62/820,866, filed on Mar. 20, 2019.

(30) Foreign Application Priority Data

Mar. 18, 2019 (IL) .......................... 265451

(51) Int. Cl.
*C12Q 1/6858* (2018.01)
*G01N 33/49* (2006.01)

(52) U.S. Cl.
CPC ......... *C12Q 1/6858* (2013.01); *G01N 33/491* (2013.01)

(58) Field of Classification Search
CPC .... C12Q 1/6858; C12Q 1/6809; C12Q 1/683; C12Q 1/6886; C12Q 2521/331; C12Q 2600/154; C12Q 2537/165; C12Q 2545/114; C12Q 2527/137; G01N 33/491
See application file for complete search history.

(56) References Cited

U.S. PATENT DOCUMENTS

| | | |
|---|---|---|
| 6,764,822 B1 | 7/2004 | Butler et al. |
| 6,812,339 B1 | 11/2004 | Venter et al. |
| 9,458,503 B2 | 10/2016 | Wasserstrom et al. |
| 9,476,100 B1 | 10/2016 | Frumkin et al. |

(Continued)

FOREIGN PATENT DOCUMENTS

| | | |
|---|---|---|
| CA | 2699606 A1 | 3/2009 |
| CN | 102037140 A | 4/2011 |

(Continued)

OTHER PUBLICATIONS

Anagnostou et al., Dynamics of Tumor and Immune Responses during Immune Checkpoint Blockade in Non-Small Cell Lung Cancer. Cancer Res. Mar. 15, 2019;79(6):1214-1225.

(Continued)

*Primary Examiner* — Jill A Warden
*Assistant Examiner* — Michael Paul Shimek
(74) *Attorney, Agent, or Firm* — Michael A. Whittaker

(57) ABSTRACT

Methods and systems for highly sensitive detection of methylation changes in DNA samples are provided, particularly in DNA samples obtained from biological fluids such as plasma and urine.

28 Claims, 6 Drawing Sheets

Specification includes a Sequence Listing.

(56) References Cited

U.S. PATENT DOCUMENTS

| | | | |
|---|---|---|---|
| 9,752,187 | B2 | 9/2017 | Wasserstrom et al. |
| 9,783,850 | B2 | 10/2017 | Frumkin et al. |
| 10,490,299 | B2 | 11/2019 | Bartling et al. |
| 11,434,528 | B2 * | 9/2022 | Frumkin .............. C12Q 1/6809 |
| 2002/0152035 | A1 | 10/2002 | Perlin |
| 2004/0181048 | A1 | 9/2004 | Wang |
| 2005/0153316 | A1 | 7/2005 | Jeddeloh et al. |
| 2005/0158739 | A1 | 7/2005 | Jeddeloh et al. |
| 2005/0272065 | A1 | 12/2005 | Lakey et al. |
| 2007/0092883 | A1 | 4/2007 | Schouten et al. |
| 2007/0178506 | A1 | 8/2007 | Martienssen et al. |
| 2007/0202526 | A1 | 8/2007 | Nakami et al. |
| 2007/0207195 | A1 | 9/2007 | Yarosh et al. |
| 2007/0275402 | A1 | 11/2007 | Lo et al. |
| 2008/0153099 | A1 | 6/2008 | Allen et al. |
| 2008/0286773 | A1 | 11/2008 | Bender |
| 2009/0018031 | A1 | 1/2009 | Trinklein et al. |
| 2009/0053706 | A1 | 2/2009 | Laird et al. |
| 2009/0175827 | A1 | 7/2009 | Byrom et al. |
| 2009/0305234 | A1 | 12/2009 | Olek et al. |
| 2010/0317000 | A1 | 12/2010 | Zhu |
| 2013/0084571 | A1 | 4/2013 | Wasserstrom et al. |
| 2014/0113286 | A1 | 4/2014 | Chan et al. |
| 2020/0035330 | A1 | 1/2020 | Bartling et al. |

FOREIGN PATENT DOCUMENTS

| | | |
|---|---|---|
| CN | 102653787 A | 9/2012 |
| CN | 107406874 A | 11/2017 |
| CN | 109312404 A | 2/2019 |
| EP | 1213360 A1 | 6/2002 |
| EP | 1748080 A2 | 1/2007 |
| EP | 2071035 A1 | 6/2009 |
| JP | 2011505132 A | 2/2011 |
| JP | 2012521769 A | 9/2012 |
| JP | 2013513379 A | 4/2013 |
| WO | 0212328 A2 | 2/2002 |
| WO | 2005040399 A2 | 5/2005 |
| WO | 2007018601 A1 | 2/2007 |
| WO | 2008038833 A1 | 4/2008 |
| WO | 2008097543 A2 | 8/2008 |
| WO | 2008104002 A2 | 8/2008 |
| WO | 2008140532 A1 | 11/2008 |
| WO | 2009083989 A1 | 7/2009 |
| WO | 2011070441 A2 | 6/2011 |
| WO | 2011101728 A2 | 8/2011 |
| WO | 2012070037 A2 | 5/2012 |
| WO | 2013055530 A1 | 4/2013 |
| WO | 2014193964 A2 | 12/2014 |
| WO | 2015159292 A2 | 10/2015 |
| WO | 2015159293 A2 | 10/2015 |
| WO | 2016024182 A1 | 2/2016 |
| WO | 2017006317 A1 | 1/2017 |
| WO | 2017043497 A1 | 3/2017 |
| WO | 2019142193 A1 | 7/2019 |
| WO | 2019162941 A1 | 8/2019 |

OTHER PUBLICATIONS

Bergman and Cedar, DNA methylation dynamics in health and disease. Nat Struct Mol Biol. Mar. 2013;20 (3):274-281.

Bock et al., Quantitative comparison of DNA methylation assays for biomarker development and clinical applications. Nat Biotechnol. Jul. 2016;34(7):726-737.

Brahmer et al., The Society for Immunotherapy of Cancer consensus statement on immunotherapy for the treatment of non-small cell lung cancer (NSCLC). J Immunother Cancer. Jul. 17, 2018;6(1):75 (15 pages).

Burdett et al., Pre-operative chemotherapy improves survival and reduces recurrence in operable non-small cell ung cancer: Preliminary results of a systematic review and meta-analysis of individual patient data from 13 randomised trials. J Thorac Oncol. 2011;6(Suppl 2):374-375.

Cacabelos, Epigenetic Biomarkers in Cancer. Clin Med Biochemistry. 2015;1(1): e101 (3 pages).

Cascone et al., A phase I study of neoadjuvant cisplatin (C), docetaxel (D) and nintedanib (N) for resectable non-small cell lung cancer (NSCLC). J Clin Oncol. 2018;36(15 suppl): abstr 8555.

Cascone et al., Induction Cisplatin Docetaxel Followed by Surgery and Erlotinib in Non-Small Cell Lung Cancer. Ann Thorac Surg. Feb. 2018;105(2):418-424.

Chen et al., Cancer-associated fibroblasts regulate the plasticity of lung cancer stemness via paracrine signalling. Nat Commun. Mar. 25, 2014;5:3472 (17 pages).

Chorostowska-Wynimko et al., Lung EpiCheckTM—results of the training and test sets of a methylation-based blood test for early detection of lung cancer. The International Association for the Study of Lung Cancer (IASLC) 19th World Conference on Lung Cancer, Sep. 23-26, 2018 Toronto, Canada; pp. 550-551 including poster (3 pages total).

Costa et al., Three Epigenetic Biomarkers, GDF15, TMEFF2, and VIM, Accurately Predict Bladder Cancer from DNA-Based Analyses of Urine Samples. Clin Cancer Res. Dec. 1, 2010;16(23):5842-5851.

Cottrell et al., A real-time PCR assay for DNA-methylation using methylation-specific blockers. Nucleic Acids Res. Jan. 13, 2004;32(1):e10 (8 pages).

Cottrell et al., Pathologic features of response to neoadjuvant anti-PD-1 in resected non-small-cell lung carcinoma: a proposal for quantitative immune-related pathologic response criteria (irPRC). Ann Oncol. Aug. 1, 2018;29 (8):1853-1860.

Di Meo et al., Liquid biopsy: a step forward towards precision medicine in urologic malignancies. Mol Cancer. Apr. 14, 2017;16(1):80 (14 pages).

Dulaimi et al., Detection of Bladder Cancer in Urine by a Tumor Suppressor Gene Hypermethylation Panel. Clin Cancer Res. Mar. 15, 2004;10(6):1887-1893.

Eads et al., MethyLight: a high-throughput assay to measure DNA methylation. Nucleic Acids Res. Apr. 15, 2000;28(8): E32.

Ehrich et al., Cytosine Methylation Profiles as a Molecular Marker in Non-Small Cell Lung Cancer. Cancer Res. Nov. 15, 2006;66(22):10911-10918.

Fantappie et al., Lack of DNA Methylation in Schistosoma mansoni. Exp Parasitol. Jul. 2001;98(3):162-166.

Forde et al., Neoadjuvant PD-1 Blockade in Resectable Lung Cancer. N Engl J Med. May 24, 2018;378 (21):1976-1986 with correction (12 pages total).

Fouse et al., Genome-scale DNA methylation analysis. Epigenomics. Feb. 2010;2(1):105-117.

Frumkin et al., Authentication of forensic DNA samples. Forensic Sci Int Genet. Feb. 2010;4(2):95-103.

Frumkin et al., DNA methylation-based forensic tissue identification. Forensic Sci Int Genet. Nov. 2011;5(5):517-524.

Greiner and Rubocki, Effectiveness of Capillary Electrophoresis Using Fluorescent-Labeled Primers in Detecting T-Cell Receptor γ Gene Rearrangements. J Mol Diagn. Aug. 2002;4(3):137-143.

Hashimoto et al., Improved quantification of DNA Methylation Using Methylation-Sensitive Restriction Enzymes and Real-Time PCR. Epigenetics. Apr.-Jun. 2007;2(2):86-91.

Hauser et al., Serum DNA Hypermethylation in Patients with Bladder Cancer: Results of a Prospective Multicenter Study. Anticancer Res. Mar. 2013;33(3):779-784.

Hegi et al., MGMT Gene Silencing and Benefit from Temozolomide in Glioblastoma. N Engl J Med. Mar. 10, 2005;352 (10):997-1003.

Heller et al., Lung cancer: From single-gene methylation to methylome profiling. Cancer Metastasis Rev. Mar. 2010;29(1):95-107.

Herman et al., Methylation-specific Pcr: A novel PCR assay for methylation status of CpG islands. Proc Natl Acad Sci U S A. Sep. 3, 1996;93(18):9821-9826.

Holemon et al., MethylScreen: DNA methylation density monitoring using quantitative PCR. Biotechniques. Nov. 2007;43(5):683-693.

Hoque et al., Quantitation of Promoter Methylation of Multiple Genes in Urine DNA and Bladder Cancer Detection. J Natl Cancer Inst. Jul. 19, 2006;98(14):996-1004.

(56) References Cited

OTHER PUBLICATIONS

Hua et al., Quantitative methylation analysis of multiple genes using methylation-sensitive restriction enzyme-based quantitative PCR for the detection of hepatocellular carcinoma. Exp Mol Pathol. Aug. 2011;91(1):455-460.

Huang et al., Quantitative analysis of multiple methylated genes in plasma for the diagnosis and prognosis of hepatocellular carcinoma. Exp Mol Pathol. Dec. 2011;91(3):702-707.

Huang et al., Quantitation of Plasma Circulating DNA Using Quantitative PCR for the Detection of Hepatocellular Carcinoma. Pathol Oncol Res. Apr. 2012;18(2):271-276.

Imperiale et al., Multitarget Stool DNA Testing for Colorectal-Cancer screening. N Engl J Med. Apr. 3, 2014;370 (14):1287-1297.

Jones and Baylin, The fundamental role of epigenetic events in cancer. Nat Rev Genet. Jun. 2002;3(6):415-428.

Katoh et al., Epigenetic Silencing of HOPX Promotes Cancer Progression in Colorectal Cancer. Neoplasia. Jul. 2012;14(7):559-571.

Kim et al., Prognostic and predictive value of VHL gene alteration in renal cell carcinoma: a meta-analysis and review. Oncotarget. Feb. 21, 2017;8(8):13979-13985.

Kim et al., Combined genomic and epigenomic assessment of cell-free circulating tumor DNA (ctDNA) improves assay sensitivity in early-stage colorectal cancer (CRC) [abstract]. In: Proceedings of the American Association for Cancer Research Annual Meeting Mar. 29-Apr. 3, 2019; Atlanta, GA. Philadelphia (PA): AACR; Cancer Res.; 79(13 Suppl): Abstract nr 916 (2 pages).

Klutstein et al., DNA Methylation in Cancer and Aging. Cancer Res. Jun. 15, 2016;76(12):3446-3450.

Kristensen and Hansen, PCR-Based Methods for Detecting Single-Locus DNA Methylation Biomarkers in Cancer Diagnostics, Prognostics, and Response to Treatment. Clin Chem. Aug. 2009;55(8):1471-1483.

Laird Cancer epigenetics. Hum Mol Genet. Apr. 15, 2005;14 Spec No. 1:R65-R76.

Lam et al., Circulating Tumor DNA Analysis with a Novel Variant Classifier for Recurrence Detection in Resected, Early-Stage Lung Cancer. J Thoracic Oncol. Sep. 2018;13(10S): S438 (abstract MA23.02).

Leng et al., Defining a Gene Promoter Methylation Signature in Sputum for Lung Cancer Risk Assessment. Clin Cancer Res. Jun. 15, 2012;18(12):3387-3395.

Liang et al., APC hypermethylation for early diagnosis of colorectal cancer: a meta-analysis and literature review. Oncotarget. Jul. 11, 2017;8(28):46468-46479.

Liloglou et al., Epigenetic biomarkers in lung cancer. Cancer Lett. Jan. 28, 2014;342(2):200-212.

Lin et al., Increase sensitivity in detecting superficial, low grade bladder cancer by combination analysis of hypermethylation of E-cadherin, p16, p14, RASSF1A genes in urine. Urol Oncol. Nov.-Dec. 2010;28(6):597-602.

Lissa and Robles, Methylation analyses in liquid biopsy. Transl Lung Cancer Res. Oct. 2016;5(5):492-504.

Liu et al., Upregulation of the inwardly rectifying potassium channel Kir2.1 (KCNJ2) modulates multidrug resistance of small-cell lung cancer under the regulation of miR-7 and the Ras/MAPK pathway. Mol Cancer. Mar. 12, 2015;14:59 (20 pages).

Lorincz Cancer diagnostic classifiers based on quantitative DNA methylation. Expert Rev Mol Diagn. Apr. 2014;14 (3):293-305.

Lowe et al., A computer program for selection of oligonucleotide primers for polymerase chain reactions. Nucleic Acids Res. Apr. 11, 1990;18(7):1757-1761.

Lu et al., Methylated DNA/RNA in Body Fluids as Biomarkers for Lung Cancer. Biol Proced Online. Mar. 17, 2017;19:2 (9 pages).

Madakashira and Sadler, DNA Methylation, Nuclear Organization, and Cancer. Front Genet. Jun. 7, 2017;8:76 (7 pages).

Martin-Magniette et al., Evaluation of the gene-specific dye bias in cDNA microarray experiments. Bioinformatics. May 1, 2005;21(9):1995-2000.

Minatani et al., Prognostic Significance of Promoter DNA Hypermethylation of cysteine dioxygenase 1 (CDO1) Gene In Primary Breast Cancer. PLoS One. Jan. 19, 2016;11(1):e0144862 (13 pages).

Moss et al., Comprehensive human cell-type methylation atlas reveals origins of circulating cell-free DNA in health and disease. Nat Commun. Nov. 29, 2018;9(1):5068 (12 pages).

Nakayashiki et al., Studies on differentially methylated parental allele in imprinted genes. Forensic Science International: Genetics Supplement Series I. 2008;(1):572-573.

Nouzova et al., Epigenomic Changes during Leukemia Cell Differentiation: Analysis of Histone Acetylation and Cytosine Methylation Using CpG Island Microarrays. J Pharmacol Exp Ther. Dec. 2004;311(3):968-981.

NSCLC Meta-analysis Collaborative Group, Preoperative chemotherapy for non-small-cell lung cancer: a systematic review and meta-analysis of individual participant data. Lancet. May 3, 2014;383(9928):1561-1571.

Oakes et al., Evaluation of a quantitative DNA methylation analysis technique using methylation-sensitive/dependent restriction enzymes and real-time PCR. Epigenetics. Jul.-Sep. 2006;1(3):146-152.

Park et al., Genome-wide epigenetic modifications in cancer. Prog Drug Res. 2011;67:25-49.

Parra et al., Effect of neoadjuvant chemotherapy on the immune microenvironment in non-small cell lung carcinomas as determined by multiplex immunofluorescence and image analysis approaches. J Immunother Cancer. Jun. 6, 2018;6 (1):48 (11 pages).

Pataer et al., Histopathologic Response Criteria Predict Survival of Patients with Resected Lung Cancer After Neoadjuvant Chemotherapy. J Thorac Oncol. May 2012;7(5):825-832.

Peng et al., Non-blood circulating tumor DNA detection in cancer. Oncotarget. Aug. 4, 2017;8(40):69162-69173.

Pignon et al., Lung adjuvant cisplatin evaluation: a pooled analysis by the LACE Collaborative Group. J Clin Oncol. Jul. 20, 2008;26(21):3552-3559.

Pisters et al., Surgery With or Without Preoperative Paclitaxel and Carboplatin in Early-Stage Non-Small-Cell Lung Cancer: Southwest Oncology Group Trial S9900, an Intergroup, Randomized, Phase III Trial. J Clin Oncol. Apr. 10, 2010;28(11):1843-1849.

Qu et al., Pathologic Assessment After Neoadjuvant Chemotherapy for NSCLC: Importance and Implications of Distinguishing Adenocarcinoma From Squamous Cell Carcinoma. J Thorac Oncol. Mar. 2019;14(3):482-493.

Rauch et al., High-resolution mapping of DNA hypermethylation and hypomethylation in lung cancer. Proc Natl Acad Sci U S A. Jan. 8, 2008;105(1):252-257.

Reinert et al., Comprehensive Genome Methylation Analysis in Bladder Cancer: Identification and Validation of Novel Methylated Genes and Application of These as Urinary Tumor Markers. Clin Cancer Res. Sep. 1, 2011;17 (17):5582-5592. With supplementary material (11 pages total).

Reinert et al., Diagnosis of Bladder Cancer Recurrence Based on Urinary Levels of EOMES, HOXA9, POU4F2, TWIST1, VIM, and ZNF154 Hypermethylation. PLoS One. 2012;7(10):e46297 (9 pages).

Rubin et al., Alu repeated DNAs are differentially methylated in primate germ cells. Nucleic Acids Res. Nov. 25, 1994;22(23):5121-5127.

Sakamoto et al., Cell type-specific methylation profiles occurring disproportionately in CpG-less regions that delineate developmental similarity. Genes Cells. Oct. 2007;12(10):1123-1132.

Smith et al., Profiling Bladder Cancer Organ Site-Specific Metastasis Identifies LAMC2 as a Novel Biomarker of Hematogenous Dissemination. Am J Pathol. Feb. 2009;174(2):371-379.

Stahlberg et al., Simple, multiplexed, PCR-based barcoding of DNA enables sensitive mutation detection in liquid biopsies using sequencing. Nucleic Acids Res. Jun. 20, 2016;44(11):e105 (7 pages).

Tost, DNA methylation signatures in circulating cell-free DNA for the monitoring of at-risk populations progressing to lung cancer. EBioMedicine. Aug. 8, 2015;2(8):798-799.

Tost, Current and Emerging Technologies for the Analysis of the Genome-Wide and Locus-Specific DNA Methylation Patterns. Adv Exp Med Biol. 2016;945: 343-430.

(56) References Cited

OTHER PUBLICATIONS

Touchman et al., Genbank accession No. G54325.1, CBS16 Human EGreen *Homo sapiens* STS genomic, sequence tagged site, Aug. 23, 1999 (online). Retrieved on Feb. 20, 2011 (Feb. 20, 2011). Retrieved from the Internet: URL: http://www.ncbi.nlm.nih.gov/nuccore/G54325.1.

Um et al., Bronchial biopsy specimen as a surrogate for DNA methylation analysis in inoperable lung cancer. Clin Epigenetics. Dec. 20, 2017;9:131 (10 pages).

Ushiku et al., Homeobox-Only Protein Expression Is a Critical Prognostic Indicator of Pancreatic Neuroendocrine Tumor and Is Regulated by Promoter DNA Hypermethylation. Pancreas. Oct. 2016;45(9):1255-1262.

Vaissiere et al., Quantitative Analysis of DNA Methylation Profiles in Lung Cancer Identifies Aberrant DNA Methylation of Specific Genes and Its Association with Gender and Cancer Risk Factors. Cancer Res. Jan. 1, 2009;69 (1):243-252.

Van Kessel et al., Evaluation of an Epigenetic Profile for the Detection of Bladder Cancer in Patients with Hematuria. J Urol. Mar. 2016;195(3):601-607.

Von Kanel et al., Quantitative one-step DNA methylation analysis (qOSMA) using native genomic DNA as template (online). Advances in Genomics Jan. 28, 2010 (retrieved Nov. 22, 2011), available on the Internet: URL: http://www.advances-in-genomics.org/presentations vonKanel.pdf (17 pages).

Warton and Samimi ,Methylation of cell-free circulating DNA in the diagnosis of cancer. Front Mol Biosci. Apr. 22, 2015;2:13.

Warton et al., Methylated circulating tumor DNA in blood: power in cancer prognosis and response. Endocr Relat Cancer. Mar. 2016;23(3):R157-R171.

Weissferdt et al., Agreement on Major Pathological Response in NSCLC Patients Receiving Neoadjuvant Chemotherapy. Clin Lung Cancer. Jul. 2020;21(4):341-348.

Wielscher et al., Diagnostic Performance of Plasma DNA Methylation Profiles in Lung Cancer, Pulmonary Fibrosis and COPD. EBioMedicine. Jul. 2, 2015;2(8):929-936.

Witte et al., Pan-cancer patterns of DNA methylation. Genome Med. Aug. 30, 2014;6(8):66 (18 pages).

Wittenberg et al., Validation of the high-throughput marker technology DArT using the model plant *Arabidopsis thaliana*. Mol Genet Genomics. Aug. 2005;274(1):30-39.

Yagi et al., DNA methylation profile of tissue-dependent and differentially methylated regions (T-DMRs) in mouse promoter regions demonstrating tissue-specific gene expression. Genome Res. Dec. 2008;18(12):1969-1978.

Yamagata et al., Aberrant DNA methylation status in human uterine leiomyoma. Mol Hum Reprod. Apr. 2009;15 (4):259-267.

Yamashita et al., Detection of Methylated CDO1 in Plasma of Colorectal Cancer; A Pcr Study. PLoS One. Dec. 3, 2014;9(12):e113546 (14 pages).

Yokoi et al., Analysis of DNA Methylation Status in Bodily Fluids for Early Detection of Cancer. Int J Mol Sci. Mar. 30, 2017;18(4):735 (25 pages).

Young et al., A cross-sectional study comparing a blood test for methylated BCAT1 and IKZF1 tumor-derived DNA with CEA for detection of recurrent colorectal cancer. Cancer Med. Oct. 2016;5(10):2763-2772.

Zeschnigk et al., IGF2/H19 hypomethylation in Silver-Russell syndrome and isolated hemihypoplasia. Eur J Hum Genet. Mar. 2008;16(3):328-334.

Zhao et al., Study on the application of parent-of-origin specific DNA methylation markers to forensic genetics. Forensic Sci Int. Nov. 25, 2005;154(2-3):122-127.

Zheng et al., Promoter hypermethylation of Wnt inhibitory factor-1 in patients with lung cancer. Medicine (Baltimore). Dec. 2016;95(49):e5433.

Zilberman and Henikoff, Genome-wide analysis of DNA methylation patterns. Development. Nov. 2007;134 (22):3959-3965.

Zou et al., Quantification of Methylated Markers with a Multiplex Methylation-Specific Technology. Clin Chem. Feb. 2012;58(2):375-383.

Ota et al., *Homo sapiens* KCNJ2 antisense RNA 1 (head to head) (KCNJ2-AS1), long non-coding RNA. Genbank: NR_036534.1, Nov. 5, 2013 (Nov. 5, 2013). URL: https://www.ncbi.nlm.nih.gov/nuccore/303227915; 2 pages.

Statland et al.,*Homo sapiens* potassium voltage-gated channel subfamily J member 2 (KCNJ2), RefSeqGene (LRG_328) on chromosome 17.Genbank: NG_008798.1, Feb. 7, 2016 (Feb. 7, 2016). URL:https://www.ncbi.nlm.nih.gov/nucleotide/209969779?report=genbank&log$=nuclalign&blast_rank=2&RID=VV2JJWYR01R; 6 pages.

Von Kanel et al., Quantitative 1-Step DNA Methylation Analysis with Native Genomic DNA as Template. Clin Chem. Jul. 2010;56(7):1098-1106.

Roberts RJ and Halford SE (1993) Type II Restriction Endonucleases. In: Linn SM, Lloyd RS and Roberts RJ (eds), Nucleases, 2nd edition. Cold Spring Harbor Laboratory Press, Cold Spring Harbor, NY, US, pp. 35-88.

Florl et al., DNA methylation and the mechanisms of CDKN2A inactivation in transitional cell carcinoma of the urinary bladder. Lab Invest. Oct. 2000;80(10):1513-1522.

Gonzalgo et al., The role of deoxyribonucleic acid methylation in development, diagnosis, and prognosis of bladder cancer. Urol Oncol. May-Jun. 2007;25(3):228-235.

Kandimalla et al., DNA methylation-based biomarkers in bladder cancer. Nat Rev Urol. Jun. 2013;10(6):327-335.

Scher et al., Detecting DNA methylation of the BCL2, CDKN2A and NID2 genes in urine using a nested methylation specific polymerase chain reaction assay to predict bladder cancer. J Urol. Dec. 2012; 188(6):2101-2107.

* cited by examiner

SEQUENCE LISTING

```
Sequence total quantity: 11
SEQ ID NO: 1            moltype = DNA  length = 85
FEATURE                 Location/Qualifiers
source                  1..85
                        mol_type = genomic DNA
                        organism = Homo sapiens
SEQUENCE: 1
agtagcgccc actgagcggt ttttcagttg ctgcaccgtt cttagcgccc aacggaacgt    60
ttcccgtacg cggagtccat aagtt                                          85

SEQ ID NO: 2            moltype = DNA  length = 69
FEATURE                 Location/Qualifiers
source                  1..69
                        mol_type = genomic DNA
                        organism = Homo sapiens
SEQUENCE: 2
cggtcccgca gcgcccgcca cacacccgcg ccagaggtcc agcgcatgtg cagtgaaatg    60
gcctagccc                                                            69

SEQ ID NO: 3            moltype = DNA  length = 72
FEATURE                 Location/Qualifiers
source                  1..72
                        mol_type = genomic DNA
                        organism = Homo sapiens
SEQUENCE: 3
cggatagcgc ggcgggcgac agccccccgg ataacccgc cgagggaggg gcgcttgtaa     60
aaccgagcgg cg                                                        72

SEQ ID NO: 4            moltype = DNA  length = 60
FEATURE                 Location/Qualifiers
source                  1..60
                        mol_type = genomic DNA
                        organism = Homo sapiens
```

```
SEQUENCE: 4
tcctccttgc cttctttcgc cgaaaggggg cgcgctcctc ccaggctgcg ctggtaccta    60

SEQ ID NO: 5            moltype = DNA   length = 78
FEATURE                 Location/Qualifiers
source                  1..78
                        mol_type = genomic DNA
                        organism = Homo sapiens
SEQUENCE: 5
aggacccgct ccgcaaagcg cccaccctcg agggaggaaa gccgagctgc gcctccgcgc    60
aaggccaggg agtgtggc                                                  78

SEQ ID NO: 6            moltype = DNA   length = 73
FEATURE                 Location/Qualifiers
source                  1..73
                        mol_type = genomic DNA
                        organism = Homo sapiens
SEQUENCE: 6
aggccgcgag cgcggcgcga tcagtagcgc ccactaacag ttcgttctgc acggcggagc    60
gcgagaccgc gga                                                       73

SEQ ID NO: 7            moltype = DNA   length = 60
FEATURE                 Location/Qualifiers
source                  1..60
                        mol_type = genomic DNA
                        organism = Homo sapiens
SEQUENCE: 7
agactaactt ttctcttgta cagaatcatc aggctaaatt tttggcatta tttcagtcct    60

SEQ ID NO: 8            moltype = DNA   length = 33
FEATURE                 Location/Qualifiers
misc_feature            1..33
                        note = Oligonucleotide
source                  1..33
                        mol_type = other DNA
                        organism = synthetic construct
SEQUENCE: 8
tcgtcggcag cgtcagatgt gtataagaga cag                                 33

SEQ ID NO: 9            moltype = DNA   length = 34
FEATURE                 Location/Qualifiers
misc_feature            1..34
                        note = Oligonucleotide
source                  1..34
                        mol_type = other DNA
                        organism = synthetic construct
SEQUENCE: 9
gtctcgtggg ctcggagatg tgtataagag acag                                34

SEQ ID NO: 10           moltype = DNA   length = 24
FEATURE                 Location/Qualifiers
misc_feature            1..24
                        note = Primer
source                  1..24
                        mol_type = other DNA
                        organism = synthetic construct
SEQUENCE: 10
ttaaaacaag atttacctct attg                                           24

SEQ ID NO: 11           moltype = DNA   length = 24
FEATURE                 Location/Qualifiers
misc_feature            1..24
                        note = Primer
source                  1..24
                        mol_type = other DNA
                        organism = synthetic construct
SEQUENCE: 11
aaatgactga atataaactt gtgg                                           24
```

METHODS AND SYSTEMS FOR DETECTING METHYLATION CHANGES IN DNA SAMPLES

CROSS-REFERENCE TO RELATED APPLICATIONS

This application is a divisional of U.S. patent application Ser. No. 17/439,906, filed Sep. 16, 2021, now U.S. Pat. No. 11,434,528, which is the United States National Phase application based on International Patent Application No. PCT/IL2020/050314 filed Mar. 17, 2020, which claims the benefit of Israel Patent Application No. 265451, filed Mar. 18, 2019, and of U.S. Provisional Application No. 62/820,866, filed Mar. 20, 2019, which applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 5, 2021, is named NUC-0004-DV1_SeqListing.txt and is 4,096 bytes in size.

FIELD OF THE INVENTION

The present invention relates to methods and systems for highly sensitive detection of methylation changes in DNA samples, particularly in DNA samples obtained from biological fluids such as plasma and urine. The systems and methods are useful for disease diagnosis.

BACKGROUND OF THE INVENTION

DNA methylation changes are known to occur in many types of cancer, including hypomethylation of isolated CpGs, and hypermethylation occurring mostly at CpG islands. Specifically, hypermethylation of CpG islands in the promotor regions of tumor suppressor genes, leading to gene silencing, has been studied extensively and demonstrated in many different types of cancer.

Tumors release DNA fragments, or "cell-free DNA", into body fluids and consequently methylation changes of tumor derived DNA molecules can be detected in "liquid biopsies" obtained from body fluids such as blood plasma and urine. In contrast to traditional biopsies, liquid biopsies are non-invasive and may better represent the full genetic spectrum of tumor sub-clones. Consequently, detection of methylation changes associated with cancer in liquid biopsies holds great promise for early detection, prognosis, and therapeutic surveillance. However, in order to detect tumor derived DNA in liquid biopsies, ultra-sensitive biochemical methods are required, because the tumor DNA can be present in extremely low quantities in relation to the large background of normal DNA.

Several techniques have been developed for detection of methylated molecules in liquid biopsies based on sodium bisulfite treatment of DNA followed by quantitative PCR, with analytical sensitivities up to 1:10,000 (Cottrell et al., *Nucleic Acids Res.*, 2004, 32(1):e10; Kristensen and Hansen, *Clin Chem.*, 2009, 55(8):1471-83; Zou et al., *Clin Chem.*, 2012, 58(2):375-83). Based on these assays, commercial products have been introduced, for detection of colorectal cancer in blood and stool, and for detection of bladder cancer in urine (Young et al. *Cancer Med.*, 2016, 5(10): 2763-72; Imperiale et al., *N Engl J Med.*, 2014, 370(14): 1287-97; Van Kessel et al., *J Urol.*, 2016, 195(3):601-7)). Despite its popularity, conversion of DNA by sodium bisulfite is a cumbersome assay, with disadvantages including degradation of the template DNA and preferable amplification of methylated or unmethylated DNA in subsequent PCR.

Another work based on bisulfite sequencing is described in Moss et al., *Nature Communications*, vol. 9, Article number: 5068 (2018), where cell-free DNA in plasma samples was analyzed using bisulfite conversion and commercial methylation arrays. Moss et al. used plasma methylation patterns to identify cell type-specific cfDNA in healthy and pathological conditions. Moss et al. assessed, inter alia, the accuracy of cancer detection using deconvolution, by performing a mixing experiment: plasma from a patient with colon cancer was mixed with plasma of healthy donors at different proportions, and the methylome of the resulting mixture was deconvoluted. The algorithm correctly identified the presence of colon DNA in the mixes, in the correct proportion, down to 3% (33-fold dilution of the original cancer plasma sample).

Non bisulfite-based methods for DNA methylation analysis include affinity/antibody enrichment or methylation-sensitive and/or -dependent restriction. Methods based on methylation-dependent restriction include differential methylation hybridization, methylated CpG island amplification and microarray, HpaII tiny fragment enrichment by ligation mediated PCR, combined bisulfite restriction analysis, and methylation-specific multiplex ligation-dependent probe amplification. These non bisulfite-based methods are mostly used for genome-wide analyses.

For analysis of specific loci, a few methods utilizing methylation-sensitive and/or -dependent restriction enzymes have been developed. For example, a method combining methylation-sensitive restriction, methylation-dependent restriction, double digest and mock digest, with subsequent quantitative PCR, was developed (Oakes et al., *Epigenetics.*, 2006, 1(3):146-52), but the requirement to perform four separate restriction and amplification reactions for each analyzed locus complicates the assay and limits its applicability in samples with a limited amount of input DNA. A similar but simpler approach employs a methylation-dependent restriction reaction followed by quantitative real-time PCR, and comparison to the same DNA sample, which was mock-digested and PCR amplified (Hashimoto et al., *Epigenetics.*, 2007, 2(2):86-95)). This approach was also used by a different team for quantitative analysis of methylation levels in hepatocellular carcinoma (Huang et al., *Exp Mol Pathol.*, 2011, 91(3):702-7). Although simpler, this approach still necessitates performing two separate digestions and PCRs for each analyzed locus. Another variant of this general technique was recently employed for detection of methylation signatures of lung cancer, pulmonary fibrosis, and COPD patients (Wielscher et al., *EBioMedicine.*, 2015, 2(8):929-36). In this variant, a single restriction reaction was performed with a methylation-sensitive enzyme, followed by two consecutive rounds of PCR amplification (a highly multiplexed initial round followed by a round of single locus PCR). The level of methylation of each locus was determined by comparing the signal obtained from that locus to signals obtained from control loci, which were amplified in separate wells. Although this approach employed only a single restriction reaction, the use of two consecutive PCR amplifications results in a rather complicated assay. In addition, the aforementioned restriction followed by amplification-based assays for methylation analysis rely on comparison of signals from different PCR wells, and this can potentially introduce a high level of noise, even if the assay is performed properly, since each well has slightly different reagent concentrations and thermal conditions.

Another method for methylation analysis that is based on methylation-sensitive and/or -dependent restriction enzymes is disclosed in WO 2011/070441, assigned to the Applicant of the present invention. More particularly, WO 2011/070441 discloses a method for categorization of a DNA sample based on methylation differences, the method comprising: (A) digesting a DNA sample with a methylation-sensitive and/or methylation-dependent restriction endonuclease; (B) performing PCR on the digested DNA to co-amplify at least two genomic loci, of which at least one is a restriction locus differentially methylated between different DNA categories; (C) determining the intensity of the signal of each amplification product; (D) calculating signal ratios between the intensities of the signals produced by the loci; and (E) comparing the signal ratios to reference values corresponding to different categories of DNA, wherein the category whose reference values correspond best to the signal ratios is determined to be the category of the DNA sample. Categories of DNA samples include, for example, DNA from different tissues and/or physiological/pathological states.

WO 2017/006317 and WO 2019/142193, assigned to the Applicant of the present invention, disclose methods for identification of bladder cancer and methods for identification of lung cancer, respectively, based on alterations in DNA methylation at selected genomic loci. The methods involve calculating signal intensity ratios between selected loci co-amplified from a tested DNA sample following digestion with at least one methylation sensitive restriction enzyme, and comparing these ratios to one or more reference ratios.

There is a need for improved methods for detecting methylation changes in DNA samples, which are more sensitive than existing methods, yet accurate. For example, improved detection of low amounts of methylated DNA molecules within a large background of non-methylated DNA is needed. Such methods are highly desired in the field of disease diagnosis, particularly cancer diagnosis based on tumor-derived circulating DNA.

SUMMARY OF THE INVENTION

The present invention provides methods and systems for detecting methylation changes in DNA samples with improved sensitivity.

The inventors of the present invention have previously developed a method for detecting methylation changes that is based on calculating signal ratios, corresponding to methylation ratios, between loci in a DNA sample. In particular, the method comprises according to some embodiments digesting the DNA sample with a methylation-sensitive or a methylation-dependent restriction endonuclease, co-amplifying from the digested DNA at least one restriction locus and a control locus (the restriction locus contains the recognition sequence of the restriction endonuclease and is differentially methylated between normal and disease DNA), determining a signal intensity for the amplification product of each locus, and calculating a ratio between the signal intensities of the restriction and control loci. The signal ratio is calculated between a restriction locus and a control locus amplified together from the same DNA sample (same template), in a single reaction mixture. The signal ratio can be compared to one or more reference ratios determined for the same restriction and control loci in DNA of a known source in order to detect methylation changes and determine whether the DNA sample is normal or derived from diseased cells, such as tumor cells.

The present invention discloses an improvement to the above method, which results in a remarkably high sensitivity in detecting methylated DNA molecules. As disclosed herein, the high sensitivity is obtained when the analyzed DNA sample (namely, the DNA sample following extraction thereof from a biological sample) is substantially devoid of single-stranded DNA. As exemplified hereinbelow, the presence of ssDNA impairs the digestion efficiency of the sample by the methylation-sensitive/-dependent restriction enzymes used in the assay. Accordingly, the ability of the assay to accurately detect methylation changes is impaired. The sensitivity that can be achieved using the improved method disclosed herein is exemplified below in an analytical setting, where methylated and unmethylated DNA molecules were mixed in different ratios. The method demonstrated methylation detection sensitivity as low as 1:200,000, namely, detection of a single methylated DNA molecule in a background of 200,000 non-methylated molecules. Such sensitivity has not been hitherto described.

The improvement disclosed herein therefore results in a method that is particularly suitable and beneficial for clinical applications requiring analysis of small amounts of methylated DNA, such as analysis of tumor-derived circulating DNA.

In some embodiments, a DNA sample that is substantially devoid of ssDNA can be obtained by extracting DNA from a tested biological sample under non-denaturing conditions and using non-denaturing reagents.

According to the methods and systems of the present invention, DNA is extracted from a biological sample, e.g., a plasma sample, to obtain DNA that is substantially devoid of ssDNA. The DNA is then subjected to methylation ratio analysis, where the DNA is digested with at least one methylation-sensitive restriction enzyme or with at least one methylation-dependent restriction enzyme, followed by co-amplification of restriction and control loci from the digested DNA. The restriction loci according to the present invention contain the recognition sequence of the at least one restriction enzyme that was used in the digestion step and are therefore cut (digested) according to their methylation level. For example, for methylation-sensitive restriction enzymes, which cleave their recognition sequence only if it is unmethylated, DNA samples with high methylation are digested to a lesser extent compared to DNA samples with low methylation, because less recognition sequences are digested within the population of DNA molecules that comprise the sample.

The restriction loci according to the present invention are differentially methylated between normal and disease DNA, for example between normal and cancer DNA. Thus, a DNA sample from a healthy subject is cut to a different extent than a DNA sample from a cancer patient. The difference in digestion efficiency establishes different amplification patterns in subsequent amplification and quantification steps. The difference in the amplification patterns allows distinguishing between DNA from a healthy subject and DNA from a patient, e.g. a cancer patient.

The amplification and quantification steps according to the methods and systems of the present invention involve co-amplification of at least one restriction locus and a control locus from the digested DNA. The control locus may be a locus that is not cut by the restriction enzyme used in the digestion step. Signal intensities of the amplified loci are then determined, and a ratio is calculated between the signal intensities of each restriction locus and the control locus. Distinct signal ratios are produced for DNA from healthy subjects and for DNA from patients, e.g., cancer patients.

The signal ratios calculated for DNA from a tested subject can be compared to one or more reference ratios determined for the same restriction and control loci in DNA samples of known sources, i.e., from healthy subjects or from patients, e.g. cancer patients. Based on the comparison, the tested sample is identified as derived from a cancer patient or from a healthy subject. It should be noted that at no point the methods and systems of the invention require determination of methylation level of individual loci per se.

According to one aspect, the present invention provides a method for sensitive detection of methylation changes in a DNA sample, the method comprising:
(a) providing a DNA sample, wherein the DNA sample contains less than 5% single-stranded DNA (ssDNA); and
(b) subjecting the DNA sample to methylation ratio analysis by digesting the DNA sample with at least one methylation-sensitive restriction endonuclease or at least one methylation-dependent restriction endonuclease, co-amplifying from the digested DNA at least one restriction locus differentially methylated between normal and disease DNA and at least one control locus, and comparing a ratio between signal intensities of the amplification products of each of said at least one restriction locus and the control locus to at least one reference ratio, thereby detecting methylation changes in the DNA sample at a detection sensitivity of at least 1:100.

In some embodiments, the DNA is cell-free DNA extracted from a biological fluid sample.

In some embodiments, the biological fluid sample is plasma, serum or urine.

In some embodiments, the DNA sample contains less than 1% ssDNA.

In some embodiments, the DNA sample contains less than 0.1% ssDNA.

In some embodiments, the DNA sample contains less than 0.01% ssDNA or is free of ssDNA.

In some embodiments, methylation changes are detected in the sample at a detection sensitivity of at least 1:500.

In additional embodiments, methylation changes are detected in the sample at a detection sensitivity of at least 1:1,000.

In some embodiments, detecting methylation changes comprises determining whether the DNA sample is a normal or disease DNA sample. In some particular embodiments, detecting methylation changes comprises determining whether the DNA sample is a normal DNA sample or a cancer DNA sample.

In some embodiments, the methylation ratio analysis in step (b) is performed using real-time PCR.

In some embodiments, the methylation ratio analysis in step (b) is performed using Next Generation Sequencing (NGS).

In some embodiments, the method comprises amplifying in step (b) a plurality of restriction loci differentially methylated between normal and disease DNA and a single control locus.

According to another aspect, the present invention provides a method for measuring methylation ratio of DNA from a human subject, the method comprising:
(a) providing a DNA sample from the human subject, wherein the DNA sample contains less than 5% single-stranded DNA (ssDNA); and
(b) subjecting the DNA sample to methylation ratio analysis by digesting the DNA sample with at least one methylation-sensitive restriction endonuclease or at least one methylation-dependent restriction endonuclease, co-amplifying from the digested DNA at least one restriction locus differentially methylated between normal and disease DNA and at least one control locus, and calculating, using software stored in non-transitory memory and implemented on a computer processor, a ratio between the signal intensities of the amplification products of each of said at least one restriction locus and the control locus,
thereby measuring methylation ratio of DNA from the human subject, with methylation detection sensitivity of at least 1:100.

According to a further aspect, the present invention provides a system for detecting methylation changes in a DNA sample, the system comprising:
(a) a DNA sample, wherein the DNA sample contains less than 5% single-stranded DNA (ssDNA); and
(b) components for carrying out a methylation ratio analysis, comprising: (i) at least one methylation-sensitive restriction endonuclease or at least one methylation-dependent restriction endonuclease for digesting the DNA sample; (ii) a plurality of primer pairs for co-amplification of a plurality of genomic loci from the DNA sample following digestion, wherein the plurality of genomic loci comprises at least one restriction locus differentially methylated between normal and disease DNA and at least one control locus; and (iii) computer software stored on non-transitory computer readable medium, the computer software directs a computer processor to determine methylation changes in the DNA sample based on a comparison of a ratio of signal intensities of the restriction locus and the control locus following amplification to a reference ratio,
with the methylation changes determined at a detection sensitivity of at least 1:100.

In some embodiments, the DNA is cell-free DNA extracted from a biological fluid sample.

In some embodiments, the biological fluid sample is plasma, serum or urine.

In some embodiments, the DNA sample contains less than 1% ssDNA.

In some embodiments, the DNA sample contains less than 0.1% ssDNA.

In some embodiments, the DNA sample contains less than 0.01% ssDNA or is free of ssDNA.

In some embodiments, the methylation changes are determined at a detection sensitivity of at least 1:500.

In additional embodiments, the methylation changes are determined at a detection sensitivity of at least 1:1,000.

In some embodiments, the plurality of loci comprises a plurality of restriction loci differentially methylated between normal and diseased DNA and a single control locus.

In some embodiments, the methylation changes are determined by performing the following steps: calculating signal intensities for amplification products of the restriction locus and the control locus; calculating a ratio between the signal intensities of the amplification products; and comparing the calculated ratio to one or more reference ratios obtained from DNA samples of known sources.

In some embodiments, determining methylation changes in the DNA sample comprises providing an indication whether the DNA sample is a normal or diseased DNA sample. In some particular embodiments, determining methylation changes in the DNA sample comprises providing an indication whether the DNA sample is a normal DNA sample or a cancer DNA sample.

In some embodiments, the components for carrying out a methylation ratio analysis further comprise a plurality of fluorescent probes for detecting the amplification products of the at least one restriction locus and the at least one control locus.

In some embodiments, the components for carrying out a methylation ratio analysis further comprise a plurality of fluorescent probes for detecting the amplification products of the at least one restriction locus and the at least one control locus.

In some embodiments, the system further comprises DNA extraction reagents to extract DNA from a biological sample, wherein the extracted DNA contains less than 5% ssDNA.

These and further aspects and features of the present invention will become apparent from the detailed description, examples and claims which follow.

DETAILED DESCRIPTION OF THE INVENTION

Figure 1:
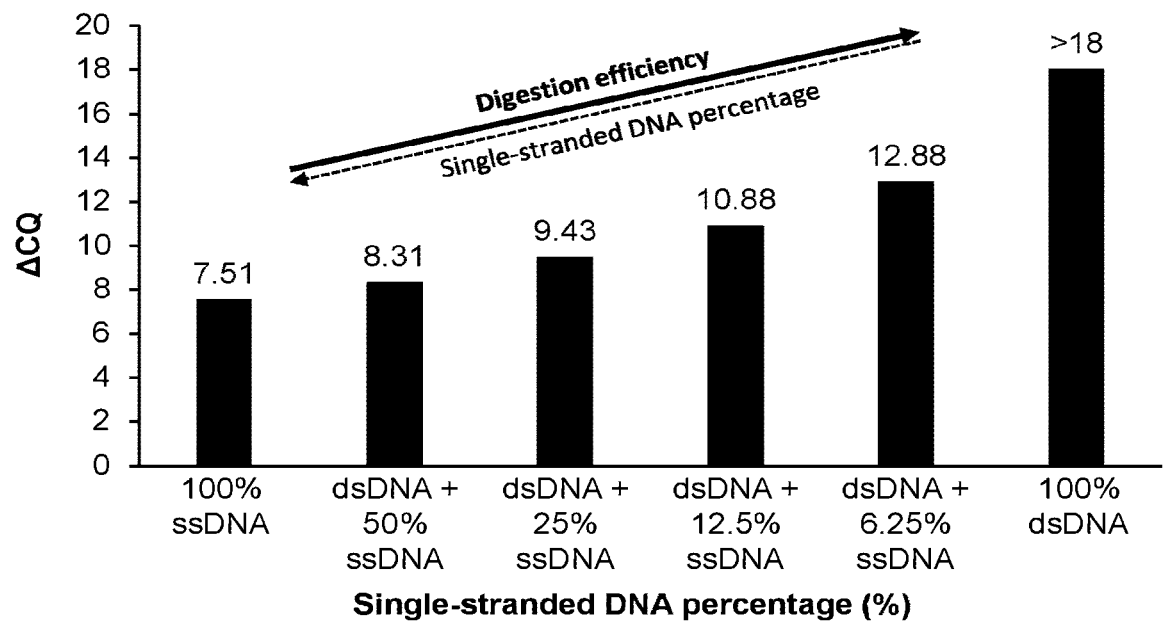
FIG. 1 shows the effect of single-stranded DNA on digestion efficacy.

The present invention relates to systems and methods for detecting methylation changes in a DNA sample with high sensitivity.

As used herein, "detecting methylation changes" refers to detecting whether a tested DNA sample contains methylation changes compared to reference DNA samples, detecting whether a DNA sample is characterized by a different methylation profile at selected genomic loci (represented herein by signal ratios between the loci) compared to a reference methylation profile, and/or determining whether the methylation profile of a DNA sample (represented herein by signal ratios between selected genomic loci) is normal or contains methylation changes indicative of the presence of a disease.

The methods and systems of the present invention detect methylation (and subsequently methylation changes) at a remarkably high detection sensitivity.

As used herein, "sensitivity", or "detection sensitivity", when referring to methylation detection, indicates the ability to detect (identify) methylated DNA molecules within a sample that contains both methylated and unmethylated DNA molecules. The detection sensitivity is presented as a ratio of the number of methylated to unmethylated molecules. For example, a 1:1,000 detection sensitivity indicates ability to detect 1 methylated DNA molecule in a background of 1,000 unmethylated DNA molecules.

In some embodiments, the detection sensitivity of the methods and systems of the present invention is at least 1:100, preferably at least 1:500, more preferably at least 1:1,000. Each possibility represents a separate embodiment of the present invention.

Example 3 hereinbelow shows an exemplary assay for determining detection sensitivity in an analytical setting (analytical sensitivity), in which DNA molecules methylated at selected genomic loci of interest are mixed with unmethylated DNA molecules at different ratios, and the ability to detect the methylated DNA molecules is tested. The methylated DNA molecules may be obtained, for example, from cell lines in which the selected genomic loci are methylated. The unmethylated DNA molecules may be artificial DNA molecules that are completely unmethylated, for example, DNA molecules obtained by cloning the selected genomic loci into plasmids.

As exemplified hereinbelow, the method according to the present invention was able to detect methylated DNA molecules at a detection sensitivity as low as 1:200,000, namely, detection of a single methylated DNA molecule in a background of 200,000 unmethylated molecules.

In some embodiments, the analytical sensitivity of the methods and systems of the present invention in detecting methylated DNA molecules (determined, for example, in an assay as described in Example 3 below) is at least 1:50,000, preferably at least 1:100,000, more preferably at least 1:200,000. Each possibility represents a separate embodiment of the present invention.

The remarkably high sensitivity is obtained according to the present invention by providing a DNA sample for analysis that is substantially devoid of single-stranded DNA.

The high sensitivity obtained by the present invention is valuable, for example, for analyzing liquid biopsy samples containing tumor-derived circulating DNA, in which the tumor DNA is usually present at extremely low amounts in relation to the background of normal DNA. High analytical sensitivity is important not only when performing the actual clinical test, but also in the development phase, when searching for potential biomarkers. Most current public data on methylation levels in samples from normal and diseased subjects were obtained using methods with high genomic coverage but relatively low analytical sensitivities. As a result, it is not possible to single out genomic loci with very low methylation levels. Therefore, methods and systems as disclosed herein are also useful for biomarker development, to identify biomarkers which "go under the radar" of conventional methylation assays.

The methods and systems of the present invention are particularly beneficial, as they provide highly sensitive and specific means for screening and/or diagnosing various diseases, such as cancer, in a non-invasive and user-independent manner.

In addition, in contrast to conventional methods utilizing methylation analysis for distinguishing between tumor-derived and normal DNA, which require determining actual methylation levels at specific genomic loci, the methodology described herein does not require to evaluate absolute methylation levels. The methods disclosed herein therefore eliminate the need for standard curves and/or additional laborious steps involved in determination of methylation levels per se, thereby offering a simple and cost-effective procedure. An additional advantage over known approaches for analyzing methylation is conferred by the signal ratios obtained by the methods of the invention, which are calculated between loci amplified from the same DNA template in the same reaction mixture (i.e., under the same reaction conditions). This renders the methods insensitive to various "noise" factors, such as changes in template DNA concentration, PCR conditions, and presence of inhibitors. Such noises are inherent for existing methods that are based on quantifying methylation levels of loci by comparing signals from separate amplification reactions.

Methylation in the human genome occurs in the form of 5-methyl cytosine and is confined to cytosine residues that are part of the sequence CG, also denoted as CpG dinucleotides (cytosine residues that are part of other sequences are not methylated). Some CG dinucleotides in the human genome are methylated, and others are not. In addition, methylation is cell and tissue specific, such that a specific CG dinucleotide can be methylated in a certain cell and at the same time unmethylated in a different cell, or methylated in a certain tissue and at the same time unmethylated in different tissues. DNA methylation is an important regulator of gene transcription.

The terms "DNA from", "DNA derived from" and the like are interchangeable and refer to DNA obtained (e.g., extracted or isolated) from a sample, e.g., a plasma sample.

According to the present invention, the DNA is obtained from accessible samples, without the need for biopsy. In some embodiments, the DNA is obtained from plasma or serum.

The term "identifying a disease (e.g. a cancer) in a subject" as used herein encompasses any one or more of screening for the disease, detecting the presence of the disease, detecting recurrence of the disease, detecting susceptibility to the disease, detecting response to treatment, determining efficacy of treatment, determining stage (severity) of the disease, determining prognosis and early diagnosis of the disease in a subject. Each possibility represents a separate embodiment of the present invention.

The term "subject" as used herein is interchangeable with "individual" and refers to a human subject. The subject may be suspected of having a certain disease. In some embodiments, the subject may be at risk of developing the disease, for example, based on previous history of the disease, genetic predisposition, and/or family history, and/or a subject who exhibits suspicious clinical signs of the disease. In some embodiments, the subject may show at least one symptom or characteristic of the disease. In other embodiments, the subject may be asymptomatic.

The term "plurality" as used herein refers to 'at least two' or 'two or more'.

In some embodiments, there is provided herein a method for sensitive detection of methylation changes in a DNA sample, the method comprising: (a) providing a DNA sample, wherein the DNA sample contains less than 5% single-stranded DNA (ssDNA); and (b) subjecting the DNA sample to methylation ratio analysis by digesting the DNA sample with at least one methylation-sensitive restriction endonuclease or at least one methylation-dependent restriction endonuclease, co-amplifying from the digested DNA at least one restriction locus differentially methylated between normal and disease DNA and at least one control locus, and comparing, using software stored in non-transitory memory and implemented on a computer processor, a ratio between signal intensities of the amplification products of each of said at least one restriction locus and the control locus to at least one reference ratio, thereby detecting methylation changes in the DNA sample at a detection sensitivity of at least 1:100.

In some embodiments, there is provided herein a method for detecting methylation changes in a DNA sample using methylation ratio analysis comprising: digesting the DNA sample with at least one methylation-sensitive restriction endonuclease or at least one methylation-dependent restriction endonuclease, co-amplifying from the digested DNA at least one restriction locus differentially methylated between normal and disease DNA and at least one control locus, and comparing a ratio between signal intensities of the amplification products of each of said at least one restriction locus and the control locus to at least one reference ratio, characterized in that the DNA sample contains less than 5% ssDNA, and in that the detection sensitivity is at least 1:100.

Plasma Sample Collection

The term "plasma" refers to the liquid remaining after a whole blood sample is subjected to a separation process to remove the blood cells. The plasma samples may be samples separated from whole blood using any method of separation, including for example by centrifugation and/or filtration. The plasma samples may be collected using conventional collection containers or tubes.

DNA Extraction

According to the present invention, the DNA sample on which the methylation analysis is carried out is substantially free of ssDNA. As used herein, "substantially free of ssDNA" or "substantially devoid of ssDNA" indicates a DNA sample in which less than 7% of the DNA is ssDNA, preferably less than 5% of the DNA is ssDNA, more preferably less than 1% of the DNA is ssDNA (namely, at least 99% of the DNA is double-stranded). In some embodiments, the DNA sample contains less than 1% ssDNA. In some embodiments, the DNA sample contains less than 0.1% ssDNA. In some embodiments, the DNA sample contains less than 0.01% ssDNA. In some embodiments, the DNA sample contains no ssDNA (free of ssDNA). Commercial kits are available for quantifying single stranded DNA in a sample. An example is the Promega QuantiFluor® kit.

In some embodiments, the DNA sample is a DNA sample extracted such that it is substantially devoid of ssDNA. In some embodiments, in order to avoid single-stranded DNA, the extraction procedure should not contain reagents that denature DNA and/or be carried out under conditions that denature DNA. Examples of DNA denaturing reagents include dimethyl sulfoxide (DMSO) and formamide. Conditions that denature DNA include chemical (for example, harsh alkaline treatment), physical (for example, sonication) and thermal (for example, temperatures above 60° C.).

Thus, in some embodiments, a DNA sample that is substantially devoid of ssDNA can be obtained by extracting DNA from a tested biological sample under non-denaturing conditions and using non-denaturing reagents. Exemplary methods are provided in the Examples section herein below.

As used herein, "non-denaturing" refers to DNA, namely, reagents and/or conditions that are non-denaturing for DNA.

Another strategy that may be employed in order to obtain a DNA sample that is substantially devoid of ssDNA is eliminating the single strands in the extracted DNA. This may be performed, for example, by treating the extracted DNA with an exonuclease I enzyme, which digests single-stranded DNA.

DNA Digestion

According to the present invention, following extraction the DNA is subjected to digestion with at least one methylation-sensitive restriction endonuclease, or at least one methylation-dependent restriction endonuclease. For example, one, two or three methylation-sensitive or methylation-dependent restriction endonucleases may be used. Each possibility represents a separate embodiment of the present invention.

In some embodiments, the entire DNA that was extracted is used in the digestion step. In some embodiments, the DNA is not quantified prior to being subjected to digestion. In other embodiments, the DNA may be quantified prior to digestion thereof.

A "restriction endonuclease", used herein interchangeably with a "restriction enzyme", refers to an enzyme that cuts DNA at or near specific recognition nucleotide sequences, known as restriction sites.

A "methylation-sensitive" restriction endonuclease is a restriction endonuclease that cleaves its recognition sequence only if it is unmethylated (while methylated sites remain intact). Thus, the extent of digestion of a DNA sample by a methylation-sensitive restriction endonuclease depends on the methylation level, where a higher methylation level protects from cleavage and accordingly results in less digestion.

A "methylation-dependent" restriction endonuclease is a restriction endonuclease that cleaves its recognition sequence only if it is methylated (while unmethylated sites remain intact). Thus, the extent of digestion of a DNA sample by a methylation-dependent restriction endonuclease depends on the methylation level, where a higher methylation level results in more extensive digestion.

In some embodiments, the at least one methylation-sensitive restriction endonuclease may be selected from the group consisting of: AatII, Acc65I, AccI, AciI, ACII, AfeI, AgeI, ApaI, ApaLI, AscI, AsiSI, AvaI, AvaII, BaeI, BanI, BbeI, BceAI, BcgI, BfuCI, BgII, BmgBI, BsaAI, BsaBI, BsaHI, BsaI, BseYI, BsiEI, BsiWI, BsII, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinPII, HpaI, HpaII, Hpy166ii, Hpy188iii, Hpy99I, HpyCH4IV, KasI, MluI, MmeI, MspAII, MwoI, NaeI, NacI, NgoNIV, Nhe-HFI, NheI, NlaIV, NotI, NotI-HF, NruI, Nt.BbvCI, Nt.B-smAI, Nt.CviPII, PaeR7I, PleI, PmeI, PmII, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI. Each possibility represents a separate embodiment of the present invention. In some particular embodiments, the at least one methylation-sensitive restriction endonuclease comprises HinP1I. In additional particular embodiments, the at least one methylation-sensitive restriction endonuclease comprises HhaI.

In some embodiments, the at least one methylation-dependent restriction endonuclease may be selected from the group consisting of: McrBC, McrA, and MrrA. Each possibility represents a separate embodiment of the present invention.

In some embodiments, the DNA is subjected to digestion with a single methylation-sensitive restriction endonuclease. In some particular embodiments, the methylation-sensitive restriction endonuclease is HinP1I. In additional particular embodiments, the methylation-sensitive restriction endonuclease may be HhaI.

In some embodiments, DNA digestion may be carried out to complete digestion. In some embodiments, the methylation-sensitive restriction endonuclease may be HinP1I, and complete digestion may be achieved following one to two hours incubation with the enzyme at 37° C. In additional embodiments, the methylation-sensitive restriction endonuclease may be HhaI, and complete digestion may be achieved following one to two hours incubation with the enzyme at 37° C.

Amplification of Genomic Loci

The terms "genomic locus" or "locus" as used herein are interchangeable and refer to a DNA sequence at a specific position on a chromosome. The specific position may be identified by the molecular location, namely, by the numbers of the starting and ending base pairs on the chromosome. As used herein, these terms also encompass the DNA sequence at the specific position along with 5' and/or 3' flanking sequences, of up to about 50 bases immediately upstream and/or downstream of said DNA sequence.

In some embodiments, the 5' flanking sequences may include between 1-50 bases. In additional embodiments, the 5' flanking sequences are of between 10-40 bases. For example, the 5' flanking sequences may include up to 10 bases, up to 15 bases, up to 20 bases, up to 25 bases, up to 30 bases, up to 35 bases, up to 40 bases, up to 45 bases, or up to 50 bases immediately upstream of the locus. Each possibility represents a separate embodiment of the present invention.

In some embodiments, the 3' flanking sequences may include between 1-50 bases. In additional embodiments, the 3' flanking sequences are of between 10-40 bases. For example, the 3' flanking sequences may include up to 10 bases, up to 15 bases, up to 20 bases, up to 25 bases, up to 30 bases, up to 35 bases, up to 40 bases, up to 45 bases, or up to 50 bases immediately downstream of the locus. Each possibility represents a separate embodiment of the present invention.

A variant of a DNA sequence at a given genomic position is called an allele. Alleles of a locus are located at identical sites on homologous chromosomes. Loci include gene sequences as well as other genetic elements (e.g., intergenic sequences).

A "restriction locus" is used herein to describe a locus that contains at least one restriction site, namely, at least one site with the recognition sequence of the at least one restriction enzyme applied in the digestion step. Restriction loci according to the present invention are differentially methylated between normal and disease DNA, meaning that for a given disease for which the analysis is carried out, for example, a certain type of cancer, the restriction loci differ in their methylation level between normal DNA and DNA derived from the cancer cells. For example, DNA from the cancer cells may have an increased methylation level at the restriction loci compared to normal non-cancerous DNA. More particularly, the restriction loci contain CG dinucleotides that are more methylated in cancer DNA compared to normal non-cancerous DNA. According to the present invention, the differentially methylated CG dinucleotides are located within recognition sites of the at least one restriction enzyme applied in the digestion step.

In some embodiments, a restriction locus according to the present invention contains at least one restriction site of a methylation-sensitive restriction enzyme, in which the CG dinucleotide is more methylated in DNA from plasma of patients with a certain type of cancer than in DNA from plasma of healthy subjects, meaning that in the plasma of the cancer patients a greater number of DNA molecules are methylated at this position compared to plasma of healthy subjects. The methylation-sensitive restriction enzyme cleaves its recognition sequence only if it is unmethylated. Thus, a DNA sample containing a higher percentage of DNA molecules in which the CG dinucleotide in the restriction site is methylated would be digested to a lesser extent compared to a DNA sample containing a higher percentage of DNA molecules in which the CG dinucleotide is unmethylated. DNA digestion by the methylation-sensitive restriction enzymes is less extensive for DNA from plasma samples of the cancer patients compared to DNA from normal (healthy) individuals. The difference in digestion efficiency establishes different amplification patterns in subsequent amplification and quantification steps, which enables distinguishing between DNA from the cancer patients and DNA from healthy subjects.

A restriction locus according to the present invention may contain additional CG dinucleotides whose methylation status is of no relevance or influence on the assay—only methylation at the recognition sequence of the restriction enzyme applied in the digestion step is relevant.

A "control locus" and "internal reference locus" are interchangeable and used herein to describe a locus, the digestion of which with the restriction enzyme applied in the digestion step is independent of the presence or absence of methylation. In some embodiments, the control locus is a locus devoid of the recognition sequence of the at least one restriction enzyme applied in the digestion step, and the sequence of the control locus remains intact regardless of its methylation status when the DNA sample is digested. Thus, the sequence of the control locus exhibits the same digestion and amplification pattern in normal and disease DNA. Advantageously, the control locus is an internal locus, i.e. a locus within the analyzed DNA sample, thus eliminating the need for external/additional control sample(s).

In some embodiments, the methods of the present invention comprise amplifying at least one restriction locus and at least one control locus following digestion of the DNA sample. As used herein, "at least one (restriction/control) locus", may encompass a single locus or a plurality of separate loci.

In some embodiments, the method comprises amplifying a plurality of restriction loci (i.e., at least two restriction loci) and a single control locus.

As used herein, "amplification" refers to an increase in the number of copies of one or more particular nucleic acid target of interest. Amplification is typically performed by polymerase chain reaction (PCR) in the presence of a PCR reaction mixture which may include a suitable buffer supplemented with the DNA template, polymerase (usually Taq Polymerase), dNTPs, primers and probes (as appropriate), as known in the art.

The term "polynucleotide" as used herein include polymeric forms of nucleotides of any length, either deoxyribonucleotides or ribonucleotides, or analogs thereof. The term "oligonucleotide" is also used herein to include a polymeric form of nucleotides, typically of up to 100 bases in length.

An "amplification product" collectively refers to nucleic acid molecules of a particular target sequence that are generated and accumulated in an amplification reaction. The term generally refers to nucleic acid molecules generated by PCR using a given set of amplification primers.

As used herein, a "primer" defines an oligonucleotide which is capable of annealing to (hybridizing with) a target sequence, thereby creating a double stranded region which can serve as an initiation point for DNA synthesis under suitable conditions. The terminology "primer pair" refers herein to a pair of oligonucleotides which are selected to be used together in amplifying a selected nucleic acid sequence by one of a number of types of amplification processes, preferably PCR. As commonly known in the art, the primers may be designed to bind to a complementary sequence under selected conditions.

The primers may be of any suitable length, depending on the particular assay format and the particular needs. In some embodiments, the primers may include at least 15 nucleotides in length, preferably between 19-25 nucleotides in length. The primers may be adapted to be especially suited to a chosen nucleic acid amplification system. As commonly known in the art, the oligonucleotide primers may be designed by taking into consideration the melting point of hybridization thereof with their targeted sequence (Sambrook et al, ibid).

In some embodiments, the restriction and control loci may be amplified from the same DNA sample (the digested sample) using pairs of reverse and forward primers designed as known in the art to specifically amplify each locus. In some embodiments, the primers may be designed to amplify a locus along with 5' and 3' flanking sequences thereof.

In some embodiments, the 5' flanking sequences may include between 1-60 bases. In additional embodiments, the 5' flanking sequences are of between 10-50 bases. For example, the 5' flanking sequences may include 10 bases, 15 bases, 20 bases, 25 bases, 30 bases, 35 bases, 40 bases, 45 bases, or 50 bases immediately upstream of the locus. Each possibility represents a separate embodiment of the present invention.

In some embodiments, the 3' flanking sequences may include between 1-60 bases. In additional embodiments, the 3' flanking sequences are of between 10-50 bases. For example, the 3' flanking sequences may include 10 bases, 15 bases, 20 bases, 25 bases, 30 bases, 35 bases, 40 bases, 45 bases, or 50 bases immediately downstream of the locus. Each possibility represents a separate embodiment of the present invention.

In some embodiments, the primers may be designed to generate amplification products of between 60-150 bps in length. In some particular embodiments, the primers may be designed to generate amplification products of between 70-140 bps in length.

In some embodiments, the method involves simultaneous amplification of more than one target sequence (at least one restriction locus and one control locus) in the same reaction mixture, a process known as multiplex amplification or co-amplification. This process requires simultaneous use of multiple primer pairs. As known in the art, the primers may be designed such that they can work at the same annealing temperature during amplification. In some embodiments, primers with similar melting temperature (Tm) are used in the method disclosed herein. A Tm variation of between about 3°-5° C. is considered acceptable for primers used in a pool.

In some embodiments, all restriction and control loci may be amplified in a single reaction mixture. In other embodiments, for example due to technical limitation of a particular machine, the digested DNA sample may be divided into several aliquots, each of which is supplemented with primer pairs for amplification of one or more restriction loci and the control locus. Thus, even if a DNA sample is divided into several aliquots, the control locus is amplified in each aliquot, and calculation of signal ratios is performed for the control locus and a restriction locus that are amplified together, i.e., from the same aliquot.

In some embodiments, amplification of the genomic loci may be carried out using real-time PCR (RT-PCR), also known as quantitative PCR (qPCR), in which simultaneous amplification and detection of the amplification products are performed.

In some embodiments, detection of the amplification products in RT-PCR may be achieved using polynucleotide probes, typically fluorescently-labeled polynucleotide probes.

As used herein, "polynucleotide probes" or "oligonucleotide probes" are interchangeable and refer to labeled polynucleotides which are complementary to specific sub-sequences within the nucleic acid sequences of loci of interest, for example, within the sequence of a restriction locus or a control locus. In some embodiments, detection is achieved by using TaqMan assays based on combined reporter and quencher molecules (Roche Molecular Systems Inc.). In such assays, the polynucleotide probes have a fluorescent moiety (fluorophore) attached to their 5' end and a quencher attached to the 3' end. During PCR amplification, the polynucleotide probes selectively hybridize to their target sequences on the template, and as the polymerase replicates the template it also cleaves the polynucleotide probes due to the polymerase's 5'-nuclease activity. When the polynucleotide probes are intact, the close proximity between the quencher and the fluorescent moiety normally results in a low level of background fluorescence. When the polynucleotide probes are cleaved, the quencher is decoupled from the fluorescent moiety, resulting in an increase of intensity of fluorescence. The fluorescent signal correlates with the amount of amplification products, i.e., the signal increases as the amplification products accumulate.

As used herein, "selectively hybridize to" (as well as "selective hybridization," "specifically hybridize to," and "specific hybridization") refers to the binding, duplexing, or hybridizing of a nucleic acid molecule (such as a primer or a probe) preferentially to a particular complementary nucleotide sequence under stringent conditions. The term "stringent conditions" refers to conditions under which a nucleic acid molecule will hybridize preferentially to its target sequence and to a lesser extent to, or not at all to, other non-target sequences. A "stringent hybridization" in the context of nucleic acid hybridization is sequence-dependent, and differs under different conditions, as known in the art.

Polynucleotide probes may vary in length. In some embodiments, the polynucleotide probes may include between 15-30 bases. In additional embodiments, the polynucleotide probes may include between 25-30 bases. In some embodiments, the polynucleotide probes may include between 20-30 bases, for example, 20 bases, 21 bases, 22 bases, 23 bases, 24 bases, 25 bases, 26 bases, 27 bases, 28 bases, 29 bases, 30 bases. Each possibility represents a separate embodiment of the present invention.

Polynucleotide probes may be designed to bind to either strand of the template. Additional considerations include the Tm of the polynucleotide probes, which should preferably be compatible to that of the primers. Computer software may be used for designing the primers and probes.

As noted above, the methods disclosed herein may involve simultaneous amplification of more than one target sequence (at least one restriction locus and one control locus) in the same reaction mixture. In order to distinguish between multiple target sequences that are amplified in parallel, polynucleotide probes labeled with distinct fluorescent colors may be used.

In some embodiments, the polynucleotide probes form fluorophore/quencher pairs as known in the art and include, for example, FAM-TAMRA, FAM-BHQ1, Yakima Yellow-BHQ1, ATTO550-BHQ2 and ROX-BHQ2.

In some embodiments, the dye combinations may be compatible to the RT-PCR thermocycler of choice.

In some embodiments, fluorescence may be monitored during each PCR cycle, providing an amplification plot showing the change of fluorescent signals from the probes as a function of cycle number.

In the context of real-time PCR, the following terminology is used:

"Quantification cycle" ("Cq") refers to the cycle number in which fluorescence increases above a threshold, set automatically by software or manually by the user. In some embodiments, the threshold may be constant for all loci and may be set in advance, prior to carrying out the amplification and detection. In other embodiments, the threshold may be defined separately for each locus after the run, based on the maximum fluorescence level detected for this locus during the amplification cycles.

"Threshold" refers to a value of fluorescence used for Cq determination. In some embodiments, the threshold value may be a value above baseline fluorescence, and/or above background noise, and within the exponential growth phase of the amplification plot.

"Baseline" refers to the initial cycles of PCR where there is little to no change in fluorescence.

Computer software may be used to analyze amplification plots and determine baseline, threshold and Cq.

In some embodiments, when a methylation-sensitive restriction enzyme is used, following digestion with the restriction enzyme, loci in which a CG dinucleotide in the enzyme's recognition site is methylated are amplified with high efficiency, because the DNA molecules are protected from digestion. The result is relatively low Cq values because detectable amplification products are shown following a relatively small (low) number of amplification cycles. Conversely, loci in which the CG dinucleotide in the enzyme's recognition site is unmethylated are cut more extensively during the digestion step, and thus result in higher Cq values in the amplification and quantification step (i.e., show detectable amplification products following a relatively high number of amplification cycles).

In alternative embodiments, amplification and detection of amplification products may be carried out by conventional PCR using fluorescently-labeled primers followed by capillary electrophoresis of amplification products. In some embodiments, following amplification the amplification products are separated by capillary electrophoresis and fluorescent signals are quantified. In some embodiments, an electropherogram plotting the change in fluorescent signals as a function of size (bp) or time from injection may be generated, wherein each peak in the electropherogram corresponds to the amplification product of a single locus. The peak's height (provided for example using "relative fluorescent units", rFU) may represent the intensity of the signal from the amplified locus. Computer software may be used to detect peaks and calculate the fluorescence intensities (peak height) of a set of loci whose amplification products were run on the capillary electrophoresis machine, and subsequently the ratios between the signal intensities.

For DNA samples digested with a methylation-sensitive restriction enzyme, loci in which the CG dinucleotide in the enzyme's recognition site is methylated produce a relatively strong signal (higher peak) in the electropherogram. Conversely, loci in which the CG dinucleotide in the enzyme's recognition site is unmethylated produce a relatively weak signal (lower peak) in the electropherogram.

In some embodiments, the fluorescent labels of the primers include any one of fluorescein, FAM, lissamine, phycoerythrin, rhodamine, Cy2, Cy3, Cy3.5, Cy5, Cy5.5, Cy7, FluorX, JOE, HEX, NED, VIC and ROX.

In additional alternative embodiments, amplification and detection of amplification products may be carried out using Next-Generation-Sequencing (NGS) technology.

Next-generation sequencing (NGS) refers to deep, high-throughput, in-parallel DNA sequencing technologies. The NGS technologies are different from the earlier Sanger sequencing method in that they provide massively parallel analysis, extremely high-throughput, from multiple samples at much reduced cost. Next-generation sequencing generally involves three basic steps: library preparation by fragmenting DNA/RNA and adding adapter sequences (e.g., by ligation or PCR), sequencing, and data analysis. Parallelized sequencing-by-synthesis or sequencing-by-ligation platforms currently employed by Illumina, Life Technologies, and Roche etc. NGS methods may also include nanopore sequencing methods or electronic detection-based methods such as Ion Torrent technology commercialized by Life Technologies.

For conducting a methylation ratio analysis using NGS, in some embodiments, following digestion of a DNA sample with at least one methylation-sensitive or methylation-dependent restriction enzyme, a sequencing library is prepared by enriching DNA fragments corresponding to the at least one restriction locus and control locus, and introducing into these DNA fragments NGS adapter sequences. "NGS adapter sequences" are oligonucleotides at the 5' and 3' ends of each DNA fragment in a sequencing library. Adapters typically include platform-specific sequences for fragment recognition by a particular sequencer: for example, sequences that enable library fragments to bind to the flow cells of Illumina platforms. Each NGS instrument provider typically uses a specific set of sequences for this purpose.

NGS adapter sequences according to some embodiments further include sample indices. "Sample indices" are sequences that enable multiple samples to be sequenced together (i.e., multiplexed) on the same instrument flow cell or chip. Each sample index, typically 6-10 bases, is specific to a given sample library and is used for de-multiplexing during data analysis to assign individual sequence reads to the correct sample. Adapters may contain single or dual sample indexes depending on the number of libraries combined and the level of accuracy desired.

In some embodiments, the NGS adapter sequences are introduced using a 2-step PCR, wherein the first PCR is carried out using primers that contain locus-specific sequences and overhang sequences that introduce a first portion of the NGS adapter sequences, and the second PCR is carried out using primers that introduce a second portion of the NGS adapter sequences and optionally sample indices.

The locus specific primers include primers specific for each of the at least one restriction locus and primers specific for the control locus.

The amplification products of the second PCR are purified and the resulting library may then be subjected to sequencing using an NGS machine (e.g., using an Illumina machine) to produce sequence reads corresponding to the restriction and control loci. The number of reads (also referred to herein as "copy number") for each locus represents the signal intensity of the locus.

In some embodiments, when a methylation-sensitive restriction enzyme is used, loci in which a CG dinucleotide in the enzyme's recognition site is methylated are protected from cleavage and the result is a relatively high copy number for these loci. Conversely, loci in which the CG dinucleotide in the enzyme's recognition site is unmethylated are cut more extensively during the digestion step, and thus result in a lower copy number.

Computer software may be used to analyze sequence reads, allocate them to target loci and quantify the number of reads (copy number).

In some embodiments, a method for detecting methylation changes in a DNA sample is provided, comprising the following steps:
  (a) subjecting the DNA sample to digestion with at least one methylation-sensitive restriction endonuclease or at least one methylation-dependent restriction endonuclease, thereby obtaining restriction endonuclease-treated DNA;
  (b) generating an NGS sequencing library from the restriction endonuclease-treated DNA, the library comprising DNA fragments corresponding to at least one restriction locus differentially methylated between normal and disease DNA and at least one control locus;
  (c) subjecting the NGS sequencing library to next-generation sequencing and determining a copy number for each of the at least one restriction locus and the control locus; and
  (d) comparing a ratio between the copy numbers of each of said at least one restriction locus and the control locus to at least one reference ratio,
  thereby detecting methylation changes in the DNA sample.

In some embodiments, a method for sensitive detection of methylation changes in a DNA sample is provided, the method comprising
  (a) providing a DNA sample substantially devoid of single-stranded DNA (ssDNA); and
  (b) subjecting the DNA sample to methylation ratio analysis by digesting the DNA sample with at least one methylation-sensitive restriction endonuclease or at least one methylation-dependent restriction endonuclease, generating an NGS sequencing library from the digested DNA, the library comprising DNA fragments corresponding to at least one restriction locus differentially methylated between normal and disease DNA and at least one control locus, and comparing a ratio between copy numbers of each of said at least one restriction locus and the control locus to at least one reference ratio,
  thereby detecting methylation changes in the DNA sample at a detection sensitivity of at least 1:100.

In some embodiments, the NGS sequencing library is generated by: (i) co-amplifying from the digested DNA at least one restriction locus differentially methylated between normal and disease DNA and at least one control locus in a single reaction mixture using locus-specific primers comprising 5' overhang sequences that introduce a first portion of NGS adapter sequences; (ii) purifying the amplification products; and (iii) conducting a second PCR that introduces NGS adapters (e.g., Illumina adapters) and optionally sample indices.

In some embodiments, the DNA is not purified between the digestion and amplification steps.

In some embodiments, an NGS-based assay as disclosed herein combines detection of methylation changes combined with mutation detection, all in one single assay. The assay advantageously allows combined analysis of small amounts of DNA in a single assay.

For a combined methylation and mutation analysis, in some embodiments, following digestion of a DNA sample with at least one methylation-sensitive or methylation-dependent restriction enzyme, a library of polynucleotides is prepared by enriching DNA fragments corresponding to the at least one restriction locus, the control locus and one or more loci for which mutation analysis is desired, and introducing into these DNA fragments NGS adapter sequences using a 2-step PCR as described above.

The locus specific primers include primers specific for the at least one restriction locus, primers specific for the control locus, and primers specific for at least one locus of interest for which mutation analysis is desired.

The amplification products of the second PCR are purified and the resulting library may then be subjected to sequencing using an NGS machine (e.g., using an Illumina machine) to produce sequence reads corresponding to the at least one restriction locus, the control locus and the at least one locus of interest for which mutation analysis is desired. Computer software may be used in order to detect sequence reads comprising one or more mutations in the locus of interest.

Signal Ratio

The term "ratio" or "signal ratio" as used herein refers to the ratio between the intensities of signals obtained from co-amplification of a pair of genomic loci in a single DNA sample (in the same reaction mixture), particularly co-amplification of a restriction locus and a control locus.

The term "signal intensity" as used herein refers to a measure reflecting the amount of locus-specific amplification products corresponding to the initial amount of intact copies of the locus. However, the signal intensity may not indicate actual amounts of amplification products/intact loci, and may not involve calculation of any absolute amounts of amplification products/intact loci. Thus, for calculating ratios of amplicon signals, no standard curve or reference DNA may be needed since it is unnecessary to calculate actual DNA concentrations or DNA methylation level per se.

In some exemplary embodiments, amplification and detection of amplification products are carried out by RT-PCR where the signal intensity of a specific locus may be represented by the Cq calculated for this locus. The signal ratio in this case may be represented by the following calculation: $2^{(Cq\ of\ control\ locus - Cq\ of\ restriction\ locus)}$.

In additional exemplary embodiments, detection of amplification products is carried out by capillary electrophoresis wherein the signal intensity of a specific locus is the number of relative fluorescence units (rfus) of its corresponding peak. The signal ratio may be calculated by dividing the heights of peaks of each restriction locus by the height of the peak of a control locus.

In additional exemplary embodiments, amplification and detection of amplification products are carried out using next-generation sequencing (NGS) where the signal intensity of a specific locus may be represented by the number of reads (copy number) calculated for this locus. The signal ratio in this case may be represented by the following calculation:

Read Number of Restriction Locus/Read Number of Control Locus

In some embodiments, calculating a ratio between signal intensities of the amplification products of a restriction locus and a control locus in a DNA sample comprises: (i) determining the signal intensity of the amplification product of the restriction locus; (ii) determining the signal intensity of the amplification product of the control locus; and (iii) calculating a ratio between the two signal intensities.

In some embodiments, calculating a ratio between signal intensities of the amplification products of a restriction locus and a control locus in the DNA sample comprises determining the Cq for each locus, and calculating the difference between the Cq of the control locus and the Cq of the restriction locus. In some embodiments, the calculating further comprises applying the following formula: $2^{(Cq\ of\ control\ locus - Cq\ of\ restriction\ locus)}$.

In additional embodiments, calculating a ratio between signal intensities of the amplification products of a restriction locus and a control locus in the DNA sample comprises determining the number of reads (copy number) for each locus, and calculating a ratio between the copy number of reads of the restriction locus and the number of reads of the control locus.

In some embodiments, calculating a signal ratio may be calculating a plurality of signal ratios, between each restriction locus and a control locus.

In some embodiments, computer software may be used for calculating a ratio between signal intensities of amplification products.

Reference Ratio

The terms "reference ratio" or "reference signal ratio" are used interchangeably and refer to a signal intensity ratio determined in DNA from a known source. A reference ratio for a given pair of restriction and control loci may be represented in a number of ways. In some embodiments, the reference ratio for a given pair of loci may be a single ratio. In some embodiments, the reference ratio for a given pair of loci may be a statistic value, such as, the mean value of a large set of reference ratios, obtained from a large set of DNA samples from a known source, e.g., mean value determined in a large group of cancer patients or a mean value determined in a large group of healthy individuals.

In other embodiments, the reference ratio for a given pair of loci may be a plurality of ratios, such as a distribution of ratios determined for this pair of loci in a large set of DNA samples from a known source. In some embodiments, the reference ratio may be a reference scale.

In some embodiments, a reference scale for a given pair of loci may include signal ratios measured for this pair of loci in a plurality of DNA samples from the same reference source. For example, a reference scale of reference cancer patients or a reference scale of reference healthy individuals. In other embodiments, a reference scale for a given pair of loci may include signal ratios from both healthy and diseased individuals, i.e. a single scale combining reference ratios from both sources. Generally, when a single scale is used, the values are distributed such that the values from the healthy individuals are at one end of the scale, e.g. below a cutoff, while the values from the patients are at the other end of the scale, e.g., above the cutoff. In some embodiments, a signal ratio calculated for a tested DNA sample from an unknown source may be compared against a reference scale of healthy and/or disease reference ratios, and a score may be assigned to the calculated signal ratio based on its relative position within the scale. In some embodiments, the higher the calculated signal ratio the higher the score assigned thereto.

The terms "disease reference ratio" (for example: "cancer reference ratio") or "reference ratio in disease DNA" (for example: "reference ratio in cancer DNA") interchangeably refer to the signal intensity ratio measured between a given restriction locus and a given control locus in DNA from samples (e.g., plasma samples) of subjects with the disease for which the analysis is carried out, for example, subjects with a certain type of cancer. The disease reference ratio represents the signal intensity ratio in disease DNA, namely, DNA from samples of subjects with the disease. The disease reference ratio may be a single ratio, a statistic value or a plurality of ratios (e.g., distribution), as detailed above.

The terms "healthy reference ratio", "normal reference ratio" or reference ratio in healthy/normal DNA" interchangeably refer to the signal intensity ratio measured between a given restriction locus and a given control locus in samples (e.g., plasma samples) from normal individuals. "Normal" or "healthy" is defined with respect to the particular disease for which the analysis is carried out. A "healthy" or "normal" individual is defined herein as an individual without detectable symptoms and/or pathological findings of the disease, as determined by conventional diagnostic methods. The healthy reference ratio represents the signal intensity ratio in normal DNA, namely, DNA from samples of healthy individuals. The healthy reference ratio may be a single ratio, a statistic value or a plurality of ratios (e.g., distribution), as detailed above.

In some embodiments, the method disclosed herein comprises pre-determination of reference ratios from disease DNA. In some embodiments, the method of the present invention comprises pre-determination of reference ratios from normal DNA.

As noted above, a signal ratio may be determined by various methods, including for example measuring peaks following capillary electrophoresis, calculating Cq values following RT-PCR, or calculating copy numbers following NGS. It is to be understood that the reference ratios and ratios measured for a tested sample of an unknown source in order to determine the presence of a certain disease are obtained using the method disclosed herein.

Disease Diagnosis

In some embodiments, the method of detecting methylation changes according to the present invention comprises identifying the presence of a certain disease in a subject, based on evaluating the signal ratios calculated for DNA from a biological sample from the subject compared to reference ratios.

In some embodiments, a method for identifying the cell source or tissue source of a DNA sample is provided (e.g., identifying whether the DNA is derived from normal or diseased cells/tissue).

A person of skill in the art would appreciate that the comparison of signal ratios calculated for a tested sample to corresponding reference signal ratios may be performed in a number of ways, using various statistical means.

In some embodiments, comparing a test signal ratio calculated for a given pair of loci to a reference signal ratio comprises comparing the test signal ratio against a single reference value. The single reference value may correspond to a mean value obtained for reference signal ratios from a large population of healthy subjects or subjects with the disease for which the analysis is carried out. In other embodiments, comparing a test signal ratio calculated for a given pair of loci to a reference signal ratio comprises comparing the test signal ratio against a distribution, or scale, of a plurality of reference signal ratios.

Known statistical means may be employed in order to determine whether the signal ratio calculated between a given restriction locus and a control locus corresponds to disease reference ratio or to normal reference ratio. In some embodiments, detecting close approximation of a calculated ratio to disease reference ratio identifies a subject as a subject having the disease. Conversely, in some embodiments, detecting close approximation of a calculated ratio to normal reference ratio identifies a subject as a subject not having the disease.

In some embodiments, disease diagnosis according to the present invention is based on analyzing whether a signal ratio of a tested DNA sample is a disease ratio, namely, indicative of a disease in question. In some embodiments, the method comprises comparing a calculated signal ratio to its corresponding healthy reference ratio (i.e., to a signal ratio determined for the same pair of loci in healthy subjects) to obtain a score (probability score) reflecting the likelihood that the calculated signal ratio is a disease ratio. In some embodiments, the method comprises comparing a calculated signal ratio to its corresponding disease reference ratio (i.e., to a signal ratio determined for the same pair of loci in subjects with the disease in question) to obtain a score reflecting the likelihood that the calculated signal ratio is a disease ratio. The better approximation of the calculated signal ratio to the disease reference ratio, the higher the score (probability score) and accordingly the likelihood that the calculated signal ratio is a disease ratio. In some embodiments, the probability score is based on the relative position of the calculated signal ratio within the distribution of disease reference ratios.

In some embodiments, the method comprises comparing a plurality of signal ratios, calculated for a plurality of restriction loci with respect to a control locus, to their corresponding healthy and/or disease references ratios.

In some embodiments, a pattern of signal ratios may be analyzed using statistical means and computerized algorithm to determine if it represents a pattern of a disease in question or a normal, healthy pattern. Exemplary algorithms are disclosed, for example, in WO 2011/070441, assigned to the Applicant of the present invention. The algorithms may include, but are not limited to, machine learning and pattern recognition algorithms In some exemplary embodiments, each calculated ratio (for each pair of restriction and control locus) may be compared against a scale of reference ratios generated for this pair from a large set of plasma samples from cancer patients, individuals not afflicted with cancer, or both. The scale may represnt signal ratios calculated between the pair of restriction locus and control locus in a large number of samples from cancer patients and/or normal individuals. The scale may exhibit a threshold value, also termed hereinafter 'cutoff' or 'pre-defined threshold', above which are reference ratios corresponding to the cancer and below are reference ratios corresponding to healthy individuals, or the other way around.

In some embodiments, the lower ratios, at the bottom of the scale and/or below a cutoff, may be from samples of normal individuals (healthy, i.e., not afflicted with the cancer in question), while the higher ratios at the top of the scale and/or above a predetermined cutoff, may be from the cancer patients. For each ratio (between each restriction locus and the control locus), a score may be given based on its relative position within the scale, and the individual scores (for each locus) are combined to give a single score. In some embodiments, the individual scores may be summed to give a single score. In other embodiments, the individual scores may be averaged to give a single score. In some embodiments, the single score may be used for determining whether the subject is having the cancer in question, where a score above a pre-defined threshold is indicative of the cancer.

In some embodiments, a score is a number between 0-100 reflecting the probability that the calculated signal ratio is a cancer ratio, wherein 0 being the lowest probability and 100 being the highest probability. In some embodiments, a threshold score is determined, wherein a score equal to or above which is indicative of the cancer. The threshold may be, for example, 60, 70 or 80. Each possibility represents a separate embodiment of the present invention.

In additional exemplary embodiments, for each calculated ratio (between each restriction locus and the control locus), the probability that it represents cancer DNA may be determined based on comparison to corresponding cancer reference ratio and/or normal reference ratio, and a score (probability score) may be allocated. Consequently, the individual probability scores calculated for each ratio (for each locus) are combined (e.g. summed or averaged) to give a combined score. The combined score may be used for determining whether the subject is having the cancer, where a combined score above a pre-defined threshold is indicative of the cancer.

Thus, in some embodiments, a threshold, or cutoff, score is determined, above (or below) which the subject is identified as having the disease in question, e.g., the type of cancer in question. The threshold score differentiates the population of healthy subjects from the population of non-healthy subject.

In some embodiments, the method of the present invention comprises providing a threshold score.

In some embodiments, determining the threshold score includes measuring signal ratios in a large population of subjects that are either healthy or have the disease in question.

In some embodiments, the threshold values are statistically significant values. Statistical significance is often determined by comparing two or more populations, and determining a confidence interval (CI) and/or a p value. In some embodiments, the statistically significant values refer to confidence intervals (CI) of about 90%, 95%, 97.5%, 98%, 99%, 99.5%, 99.9% and 99.99%, while preferred p values are less than about 0.1, 0.05, 0.025, 0.02, 0.01, 0.005, 0.001 or less than 0.0001. Each possibility represents a separate embodiment of the present invention. According to some embodiments, the p value of the threshold score is at most 0.05.

As used herein, the term "about", when referring to a measurable value is meant to encompass variations of +/−10%, more preferably +/−5%, even more preferably +/−1%, and still more preferably +/−0.1% from the specified value.

In some embodiments, the method further comprises comparing the signal ratio calculated between a given restriction locus and a control locus to its corresponding normal/healthy reference ratio to obtain a probability score, wherein detecting a low probability score for said ratio with respect to the corresponding healthy reference ratio is indicative that the subject has the disease for which the analysis is carried out.

In some embodiments, the diagnostic sensitivity of the methods disclosed herein may be at least about 75%. In some embodiments, the diagnostic sensitivity of the methods may be at least about 80%. In some embodiments, the diagnostic sensitivity of the method may be at least about 85%. In some embodiments, the diagnostic sensitivity of the methods may be at least about 90%.

In some embodiments, the "diagnostic sensitivity" of a diagnostic assay as used herein refers to the percentage of diseased individuals who test positive (percent of "true positives"). Accordingly, diseased individuals not detected by the assay are "false negatives". Subjects who are not diseased and who test negative in the assay are termed "true negatives." The "specificity" of the diagnostic assay is one (1) minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

In some embodiments, the diagnostic specificity of the methods disclosed herein may be at least about 65%. In some embodiments, the diagnostic specificity of the methods may be at least about 70%. In some embodiments, the diagnostic specificity of the method may be at least about 75%. In some embodiments, the diagnostic specificity of the methods may be at least about 80%.

Definitive Diagnosis

In some embodiments, following identification of a disease in question according to the method of the present invention, the subject may undergo definitive diagnosis of the disease. The definitive diagnosis may be carried out, for example, by biopsy.

Treatment

In some embodiments, following identification of a disease in question according to the method of the present invention, the subject may receive a suitable treatment for the disease. Thus, in some embodiments, methods of treatment are provided, comprising identifying a disease in a human subject according to the method of the present invention, and administering to said subject a suitable therapy.

Systems and Kits

In some embodiments, there is provided herein systems for detecting methylation changes in a DNA sample. In some embodiments, there is provided herein kits for detecting methylation changes in a DNA sample.

In some embodiments, the systems and kits are for detecting methylation changes in a DNA sample according to the method of the present invention.

In some embodiments, a system according to the present invention comprises: (a) a DNA sample, wherein the DNA sample is substantially devoid of ssDNA (e.g., contains less than 5% single-stranded DNA (ssDNA), for example less than 1% ssDNA); and (b) components for carrying out a methylation ratio analysis.

As used herein, "components" for carrying out a methylation ratio analysis encompass biochemical components (e.g., enzymes, primers, nucleotides), chemical components (e.g., buffers, probes), and technical components (e.g., PCR system, equipment such as tubes, vials, plates, pipettes, and also computer software stored on a computer readable medium, computer processors and the like).

In some embodiments, the components for carrying out a methylation ratio analysis comprise: (i) at least one methylation-sensitive restriction endonuclease or at least one methylation-dependent restriction endonuclease for digesting the DNA sample; (ii) a plurality of primer pairs for co-amplification of a plurality of genomic loci from the DNA sample following digestion, wherein the plurality of genomic loci comprises at least one restriction locus differentially methylated between normal and disease DNA and at least one control locus; and (iii) computer software stored on non-transitory computer readable medium, the computer software directs a computer processor to determine methylation changes in the DNA sample based on a comparison of a ratio of signal intensities of the restriction locus and the control locus following amplification to a reference ratio.

In some embodiments, the components for carrying out a methylation ratio analysis comprise machinery for carrying out the amplification and detection steps, such as a PCR machine (e.g., real-time PCR machine) and/or an NGS machine.

In some embodiments, the components for carrying out a methylation ratio analysis comprise a plurality of polynucleotide probes for detecting amplification products of the at least one restriction locus and the at least one control locus.

In some embodiments, the system comprises a processor, configured to carry out the following: determining methylation changes in the DNA sample based on comparison of a ratio of signal intensities of the restriction locus and the control locus following amplification to a reference ratio. In some embodiments, the processor is coupled to a storage storing a plurality of reference ratios.

In some embodiments, a system according to the present invention comprises: (a) at least one methylation-sensitive restriction endonuclease or at least one methylation-dependent restriction endonuclease for digesting a DNA sample, wherein the DNA sample is substantially devoid of ssDNA (e.g., contains less than 5% single-stranded DNA (ssDNA); (b) a plurality of primer pairs for co-amplification of a plurality of genomic loci from the DNA sample following digestion with the restriction endonuclease of (a), wherein the plurality of genomic loci comprises at least one restriction locus differentially methylated between normal and disease DNA and at least one control locus; and (c) computer software stored on non-transitory computer readable medium, the computer software directs a computer processor to determine methylation changes in the DNA sample based on a comparison of a ratio of signal intensities of the restriction locus and the control locus following amplification to a reference ratio, with the methylation changes determined at a detection sensitivity of at least 1:100.

In some embodiments, a kit or a system according to the present invention comprises DNA extraction reagents to extract DNA from a biological sample such that the extracted DNA is substantially devoid of ssDNA, for example contains less than 5% ssDNA, for example less than 1% ssDNA.

In some embodiments, a kit or a system according to the present invention comprises ingredients needed for DNA digestion in addition to the restriction enzyme(s), such as one or more buffers.

In some embodiments, a kit or a system according to the present invention comprises ingredients needed for amplification of loci in addition to the primers, such as a DNA polymerase, nucleotide mix and buffer(s).

In some embodiments, a kit or a system according to the present invention comprises ingredients needed for detection of amplification products, such as polynucleotide probes, e.g., fluorescently labeled polynucleotide probes.

In some embodiments, a kit or a system according to the present invention comprises instructions for carrying out the detection of methylation changes using a computer software stored on non-transitory computer-readable medium, the computer software directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is a normal DNA sample or a DNA sample derived from diseases cells, e.g., tumor cells.

In some embodiments, the kit or system further comprises a non-transitory computer readable medium storing a computer software that directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is a normal DNA sample or a DNA sample derived from diseases cells, e.g., tumor cells.

In some embodiments, a computer software according to the present invention receives as an input parameters or raw data of a real-time PCR run. In some embodiments, the computer software directs a computer processor to analyze the real-time PCR run to determine signal intensities and signal ratios.

In some embodiments, a computer software according to the present invention receives as an input sequence reads of an NGS run. In some embodiments, the computer software directs a computer processor to analyze the NGS run to determine signal intensities and signal ratios.

The computer software includes processor-executable instructions that are stored on a non-transitory computer readable medium. The computer software may also include stored data. The computer readable medium is a tangible computer readable medium, such as a compact disc (CD), magnetic storage, optical storage, random access memory (RAM), read only memory (ROM), or any other tangible medium.

It is understood that the computer-related methods, steps, processes described herein are implemented using software stored on non-volatile or non-transitory computer readable instructions that when executed configure or direct a computer processor or computer to perform the instructions.

Each of the system, server, computing device, and computer described in this application can be implemented on one or more computer systems and be configured to communicate over a network. They all may also be implemented on one single computer system. In one embodiment, the computer system includes a bus or other communication mechanism for communicating information, and a hardware processor coupled with bus for processing information.

The computer system also includes a main memory, such as a random-access memory (RAM) or other dynamic storage device, coupled to bus for storing information and instructions to be executed by processor. Main memory also may be used for storing temporary variables or other intermediate information during execution of instructions to be executed by processor. Such instructions, when stored in non-transitory storage media accessible to processor, render computer system into a special-purpose machine that is customized to perform the operations specified in the instructions.

The computer system further includes a read only memory (ROM) or other static storage device coupled to bus for storing static information and instructions for processor. A storage device, such as a magnetic disk or optical disk, is provided and coupled to bus for storing information and instructions.

The computer system may be coupled via bus to a display, for displaying information to a computer user.

An input device, including alphanumeric and other keys, is coupled to bus for communicating information and command selections to processor. Another type of user input device is cursor control, such as a mouse, a trackball, or cursor direction keys for communicating direction information and command selections to processor and for controlling cursor movement on display.

According to one embodiment, the techniques herein are performed by the computer system in response to the processor executing one or more sequences of one or more instructions contained in main memory. Such instructions may be read into main memory from another storage medium, such as storage device. Execution of the sequences of instructions contained in main memory causes the processor to perform the process steps described herein. In alternative embodiments, hard-wired circuitry may be used in place of or in combination with software instructions.

The term storage media as used herein refers to any non-transitory media that store data and/or instructions that cause a machine to operation in a specific fashion. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—the Effect of Single-Stranded DNA on Digestion Efficiency

Detection of methylation changes according to the present invention is based on methylation-sensitive or methylation-dependent enzymatic digestion of DNA, followed by amplification of target loci and analysis of the amplification signals. The following experiment tested variations in digestion efficiency when adding variable amounts of single-stranded DNA to a double-stranded DNA sample. The digestion efficacy was evaluated using real-time PCR, by the effect of various amounts of single-stranded DNA on ΔCq between a test locus and a control locus. The digestion efficacy reflects the ability of the assay to accurately detect methylation changes.

Experimental Procedure

Double-stranded DNA from A-673 cell line was spiked with increasing percentages of a synthetic single-stranded DNA oligonucleotide corresponding to the following lung-cancer associated genomic locus:

| SEQ ID NO. | Nucleic acid sequence |
|---|---|
| 3 | CGGATAGCGC GGCGGGCGAC AGCCCCCCGG ATAACCCCGC CGAGGGAGGG GCGCTTGTAA AACCGAGCGG CG |

This lung cancer test locus was previously disclosed in WO 2019/142193, assigned to the Applicant of the present invention. It comprises the recognition sequence of the methylation-sensitive restriction enzyme HhaI. The DNA from A-673 cell line is unmethylated at this test locus, and accordingly DNA from this cell line is expected to be cut extensively by HhaI at the test locus.

The spiked samples, as well as a sample of pure single-stranded DNA ("100% single-stranded DNA") and a sample of DNA from A-673 cells which was not spiked with ssDNA ("100% double-stranded DNA") were subjected to methylation-sensitive enzymatic digestion. Enzymatic digestion was performed for 2 hours at 37° C. followed by a heat inactivation of the enzyme for 20 minutes at 65° C.

Next, real-time PCR was carried out on the digested samples to amplify in each sample the test locus detailed above and a control locus as follows:

| SEQ ID NO. | Nucleic acid sequence |
|---|---|
| 7 | AGACTAACTTTTCTCTTGTACAGAATCATCAGGCTAAAT TTTTGGCATTATTTCAGTCCT |

The control locus is a locus that does not contain a recognition sequence of HhaI and remains intact when a DNA sample is digested with HhaI regardless of its methylation status.

Following digestion, each digested sample was supplemented with primer pairs for amplification of the test locus and the control locus. Each amplification reaction (total volume 25 microliter) further contained dNTPs, a DNA polymerase and a reaction buffer. To enable detection of amplification products during amplification, fluorescently-labeled polynucleotide probes (one for each locus) were added to the reaction. Real-time PCR reactions were carried out in an ABI 7500 FastDx instrument with the following PCR program: 95° C., 10 min→45×(95° C., 15 sec)→60° C., 1 min.

Following amplification, data on the level of fluorescent signals from the probes as a function of cycle number were analyzed to calculate the quantification cycle (Cq) for each locus and the ΔCq, namely, the difference between the Cq of the test locus and the Cq of the control locus.

Results

The results are summarized in Table 1 and FIG. 1. The ΔCq between the test locus and the control locus in the 100% single-stranded DNA sample was 7.51 cycles, whereas there was no visible amplification of the test locus in the 100% double-stranded DNA sample, corresponding to a ΔCq between the test locus and the control locus of >18 cycles. The ΔCq between the test locus and the control locus increased as the single-stranded DNA percentage in the sample decreased.

The increase in the ΔCq reflects a more efficient digestion of the test locus when less ssDNA was present. When less ssDNA was present, more DNA was digested, resulting in an increase in the Cq of the test locus compared to the Cq of the control locus (an increase in the cycle number in which a detectable amplification product of the test locus appeared in the assay compared to the cycle number in which a detectable amplification product appeared for the control locus).

TABLE 1

ΔCQ test locus vs. control locus

| 100% single-stranded DNA | Double-stranded DNA + 50% single-stranded DNA | Double-stranded DNA + 25% single-stranded DNA | Double-stranded DNA + 12.5% single-stranded DNA | Double-stranded DNA + 6.25% single-stranded DNA | 100% Double-stranded DNA |
|---|---|---|---|---|---|
| 7.51 | 8.31 | 9.43 | 10.88 | 12.88 | >18 |

This experiment demonstrates that the presence of single-stranded DNA in the sample impairs the digestion efficiency. The digestion efficacy reflects the ability of the assay to accurately detect methylation changes. The effect is proportional to the amount of single-stranded DNA in the sample-this effect is observable starting at 6.25% of single-stranded DNA in the sample.

Example 2—Detecting Methylation Changes at Lung Cancer-Associated Genomic Loci

The following experiment tests the effect of the presence of ssDNA in a DNA sample on the ability to detect methylation changes at lung cancer-associated genomic loci by methylation ratio analysis as described herein. The lung cancer-associated restriction loci, previously disclosed in WO 2019/142193, assigned to the Applicant of the present invention, comprise the sequences set forth below as SEQ ID NOs: 1-6.

TABLE 2

Restriction loci

| SEQ ID NO. | Nucleic acid sequence |
|---|---|
| 1 | AGTAGCGCCCACTGAGCGGTTTTTCAGTTGCTGCACCGTTCTT AGCGCCCAACGGAACGTTTCCCGTACGCGGAGTCCATAAGTT |
| 2 | CGGTCCCGCA GCGCCCGCCA CACACCCGCG CCAGAGGTCC AGCGCATGTG CAGTGAAATG GCCTAGCCC |
| 3 | CGGATAGCGC GGCGGGCGAC AGCCCCCCGG ATAACCCCGC CGAGGGAGGG GCGCTTGTAA AACCGAGCGG CG |
| 4 | TCCTCCTTGC CTTCTTTCGC CGAAAGGGGG CGCGCTCCTC CCAGGCTGCG CTGGTACCTA |
| 5 | AGGACCCGCT CCGCAAAGCG CCCACCCTCG AGGGAGGAAA GCCGAGCTGC GCCTCCGCGC AAGGCCAGGG AGTGTGGC |
| 6 | AGGCCGCGAG CGCGGCGCGA TCAGTAGCGC CCACTAACAG TTCGTTCTGC ACGGCGGAGC GCGAGACCGC GGA |

A plasma sample is obtained from a subject with no lung cancer. DNA in plasma samples from subjects with no lung cancer is mostly unmethylated at the above six restriction loci. DNA is extracted from the plasma sample using the QIAamp® Circulating Nucleic Acid Kit (QIAGEN, Hilden, Germany). This extraction procedure is carried out at a temperature at or below 60° C. and using non-denaturing reagents.

The extracted DNA is divided into aliquots, each spiked with a different percentage of synthetic single-stranded DNA oligonucleotides corresponding to each of the above restriction loci, as follows: "0 ssDNA" (no ssDNA), 0.1%, 1%, 10% ssDNA. Each aliquot is then subjected to methylation ratio analysis, as follows:

Each aliquot is digested with the methylation-sensitive restriction endonuclease HhaI. The digestion reaction (total volume 100 microliter) includes 80 microliters of the extracted DNA (not quantified) and HhaI in a digestion buffer. The digestion is carried out at 37° C. for 2 hours.

Next, real-time PCR is carried out on the digested aliquots to amplify in each aliquot the 6 restriction loci detailed above and a control locus as set forth below in SEQ ID NO: 7.

| 7 | AGACTAACTTTTCTCTTGTACAGAATCATCAGGCTAAATTT TTGGCATTATTTCAGTCCT |
|---|---|

The control locus is a locus that does not contain a recognition sequence of HhaI and remains intact when a DNA sample is digested with the restriction enzyme regardless of its methylation status.

Following digestion, each digested aliquot is divided into three (3) sub-aliquots containing 12 microliters. Each sub-aliquot is supplemented with primer pairs for amplification of two restriction loci out of the six and the control locus (the control locus is to be amplified in every sub-aliquot). Amplicons of between 77 to 139 bases are amplified. Each amplification reaction (total volume 30 microliter) further contains dNTPs and a reaction buffer. To enable detection of amplification products during amplification, fluorescently-labeled polynucleotide probes (one for each locus) are added to the reaction. The following fluorescent labels are used: FAM, JOE, ROX. Real-time PCR reactions are carried out in an ABI 7500 FastDx instrument with the following PCR program: 95° C., 10 min→45×(95° C., 15 sec)→60° C., 1 min.

Following amplification, data on the level of fluorescent signals from the probes as a function of cycle number are analyzed to calculate the quantification cycle (Cq) for each locus and the ΔCq (difference between the Cq of the restriction locus and the Cq of the control locus) of each restriction locus.

For each sample, ratios are calculated between the signal intensity of each of restriction loci 1-6 (SEQ ID NO: 1-6) and the signal intensity of the control locus (SEQ ID NO: 7), as follows: the Cq is determined for each restriction locus and for the control locus. The Cq values are used in the following formula:

$$2^{(Cq\ of\ control\ locus-Cq\ of\ restriction\ locus)}.$$

The numerical value obtained for each restriction locus with respect to the control locus represents the signal ratio (reflecting methylation ratio) between this restriction locus and the control locus. Altogether, six signal ratios were calculated for each sample.

Next, a score is calculated for each locus in each sample, the score being the signal ratio normalized in respect to reference ratios such that the highest signal ratio is scored "100" and the lowest signal ratio is scored "0". The six scores obtained for each sample are combined into a single score, termed "EpiScore", which is a number between 0 and 100, reflecting the overall relative methylation level of the sample at the panel of six restriction loci. A sample is classified as "lung cancer" if its EpiScore is above or equal to 70 (a threshold that was determined based on information from an earlier set of samples), and as "healthy" if its EpiScore was below 70.

The EpiScore calculated for the "0 ssDNA" sample represents the score of the original DNA sample following extraction thereof. As this sample is mostly unmethylated at the above restriction loci, its EpiScore is very low. The EpiScore calculated for the "0 ssDNA" sample is compared to the EpiScores calculated for the samples spiked with single-stranded DNA, demonstrating the effect of having ssDNA in the DNA sample on the accuracy of the EpiScore and accordingly on the ability of the assay to correctly distinguish between healthy and disease DNA (lung cancer DNA in this case).

Example 3—Analytical Sensitivity

The analytical sensitivity of the assay was tested on mixtures of methylated and unmethylated DNA species.

Materials and Methods

Unmethylated DNA

Unmethylated DNA contained two DNA fragments (the test locus and the internal reference, control locus), each amplified by PCR from human cell line HCT-15 DNA and cloned separately into the pGEM-T Easy vector (Promega). Plasmid DNAs were extracted using the QIAGEN Plasmid Mini Kit to obtain a DNA sample that is essentially free of single-stranded DNA (ssDNA) and quantified using Nano-Drop. Purified plasmid DNA was sequenced in order to verify the sequence of the insert. Equal molar amounts of both of the plasmid species were combined together in order to create the sample of unmethylated DNA used in the experiments.

Methylated DNA

Methylated DNA consisted of DNA extracted from the HCT-15 cell line. Cells were purchased from Sigma-Aldrich and maintained in culture for 38 generations before harvest. DNA was extracted using the Wizard Genomic DNA Purification kit (Promega) to obtain a DNA sample that is essentially free of ssDNA. Extracted DNA was quantified using NanoDrop.

Bisulfite Sequencing

Both the methylated and unmethylated DNA samples were treated with sodium bisulfite using the EpiTect Bisulfite Kit (QIAGEN). Following bisulfite conversion, the test locus was amplified from both DNA species. PCR products were then purified using the QIAquick PCR Purification Kit (QIAGEN) and sequenced.

Mixes of Methylated and Unmethylated DNA

The mixes were constructed by adding the appropriate amounts of methylated and unmethylated DNAs in order to create the desired molar ratios.

DNA Digestion

80 μl of each DNA sample were digested in 100 μl total volume with 5 μl HinP1I (New England Biolabs), 10 μl CutSmart buffer (New England Biolabs), and 5 μl DDW. Digestion was performed at 37° C. for two hours followed by 20 minutes heat inactivation at 65° C.

Real Time PCR

Each PCR well contained a total of 300, with 0.6 μl AmpliTaq Gold (Thermo Fisher), 3 μl Buffer I (Thermo Fisher), 0.6 μl 10 mM dNTP mix (Sigma-Aldrich), 0.20 μM each primer (test locus forward, test locus reverse, internal reference forward, internal reference reverse), 0.4 μM of the test probe, 0.20 μM of the internal reference probe and 12 μl of the digested DNA sample. PCR was performed in the 7500 Fast Dx real time PCR instrument (Thermo Fisher) with the following PCR program: 10 minutes at 95° C. followed by 45 cycles of 15 seconds at 95° C. and 1 minute at 60° C.

Signal Analysis

Fluorescence data from the sds file outputted from the real time PCR instrument was analyzed by a dedicated software. For each locus a Cq (cycle of quantitation) value was calculated, equal to the cycle at which the fluorescence data of the locus crossed the threshold of 50,000 fluorescence units. For each well a ΔCq value was calculated, equal to the Cq of the test locus minus the Cq of the internal reference locus.

Results

Description of the Assay

The assay includes three consecutive steps: digestion, amplification, and analysis. In the first step, a DNA sample, which is substantially free of ssDNA, is digested with a methylation-sensitive restriction enzyme. An aliquot of the digested DNA is then subjected to real time PCR amplification where two genomic loci are co-amplified. The first locus—for which the methylation level is analyzed—is called the "test locus", or "restriction locus", and it contains at least one recognition sequence of the restriction enzyme that was used in the digestion step. The second locus is a control locus, termed herein "an internal reference", which does not contain the recognition sequence of the restriction enzyme used in the digestion step. The extent of digestion of the test locus in the digestion step depends on its methylation level, where higher level of methylation results is less digestion. Higher level of methylation therefore results in more template for the real time PCR, and consequently lower Cq values (detectable amplification products are seen after a relatively low number of amplification cycles). In contrast, low methylation level results in extensive digestion and accordingly less template for the real time PCR and higher Cq values (detectable amplification products are seen after a higher number of amplification cycles). The internal reference is not recognized by the restriction enzyme and therefore remains intact regardless of its methylation levels. The amplification signals (Cq values) of the two loci are distinguished by using different fluorophores for their respective probes during PCR. In the third step, the signals are analyzed by dedicated software, which determines the ΔCq between the test and internal reference loci.

In the current experiment, the test locus is a human genomic locus on chromosome 5 that is differentially methylated between lung cancer tissues and normal lung tissues, and mostly unmethylated in normal human plasma:

(SEQ ID NO: 1)
AGTAGCGCCCACTGAGCGGTTTTTCAGTTGCTGCACCGTTC

TTAGCGCCCAACGGAACGTTTCCCGTACGCGGAGTCCATAA

GTT

A locus on human chromosome 7 was used as the internal reference:

(SEQ ID NO: 7)
AGACTAACTTTTCTCTTGTACAGAATCATCAGGCTAAATTT

TTGGCATTATTTCAGTCCT

Analytical Sensitivity of the Assay

Figure 2A:
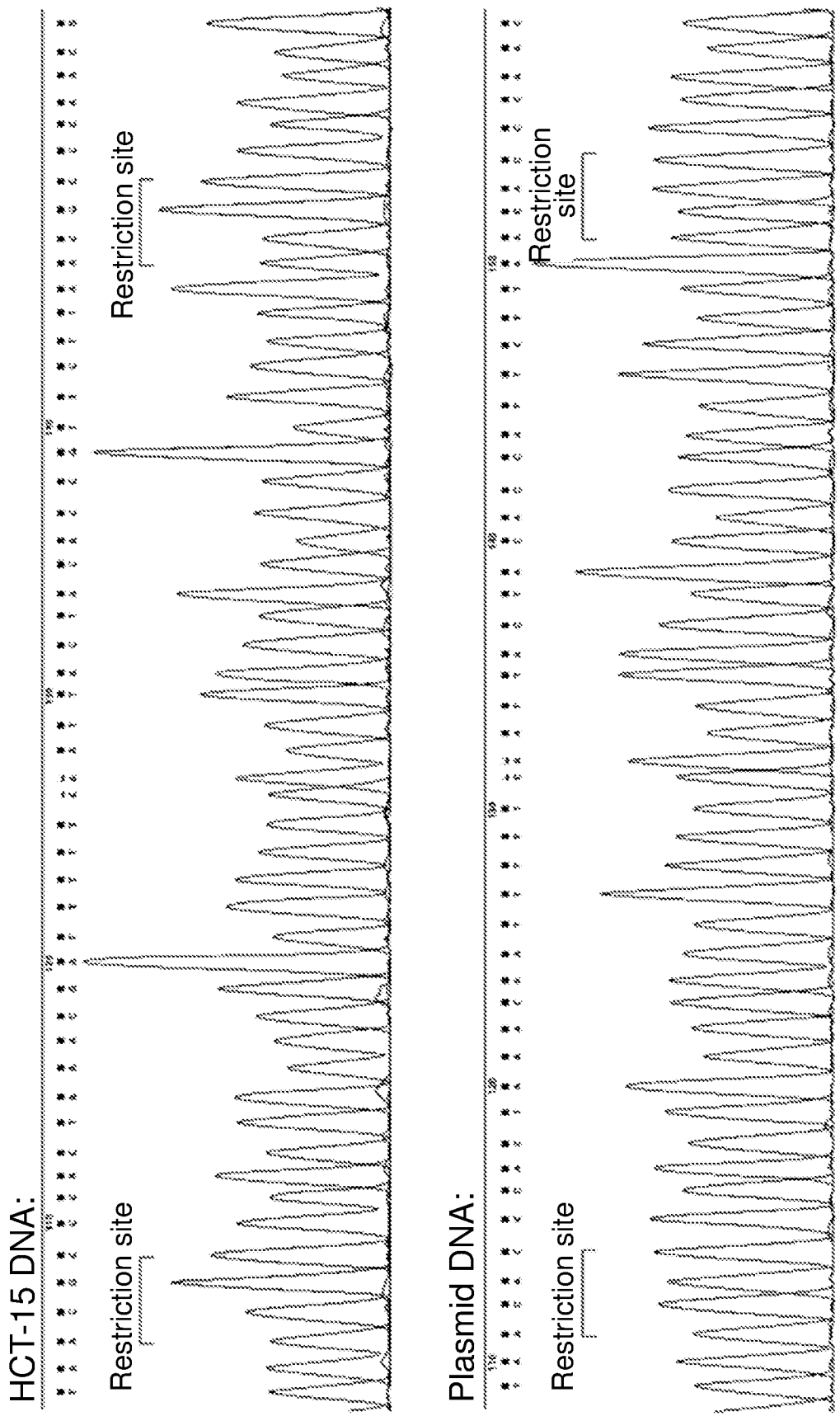
FIG. 2A shows bisulfite sequencing of the test locus in HCT-15 (methylated) and plasmid (unmethylated) DNA samples. Recognition sites of the endonuclease used in the assay are indicated.

In order to determine the analytical sensitivity of the assay, mixtures of methylated and unmethylated DNA samples with different ratios were analyzed. DNA from human cell line HCT-15 was used as the source of the methylated DNA sample, because it is methylated at the test locus, as determined by bisulfite sequencing (FIG. 2A, upper panel).

The unmethylated DNA sample was constructed from a mixture of two bacterial plasmid DNA samples, containing the test and internal reference loci as inserts. The fact that $E.$ $coli$ bacteria, which were used to produce the plasmid DNA, lack CpG methyltransferases, assures that the plasmid DNA is completely unmethylated at the test locus, as verified by bisulfite sequencing (FIG. 2A, lower panel). The methylated and unmethylated DNA species were then mixed together at molar ratios of 1:8, 1:64, 1:512, 1:4096, 1:32768, and 1:200,000 methylated:unmethylated DNA, and these mixtures were then analyzed with the above described assay. In each PCR well, the number of unmethylated DNA template molecules was 4,000,000 and the number of methylated DNA molecules varied—from 500,000 in the 1:8 mixture down to 20 molecules in the 1:200,000.

Figure 2B:
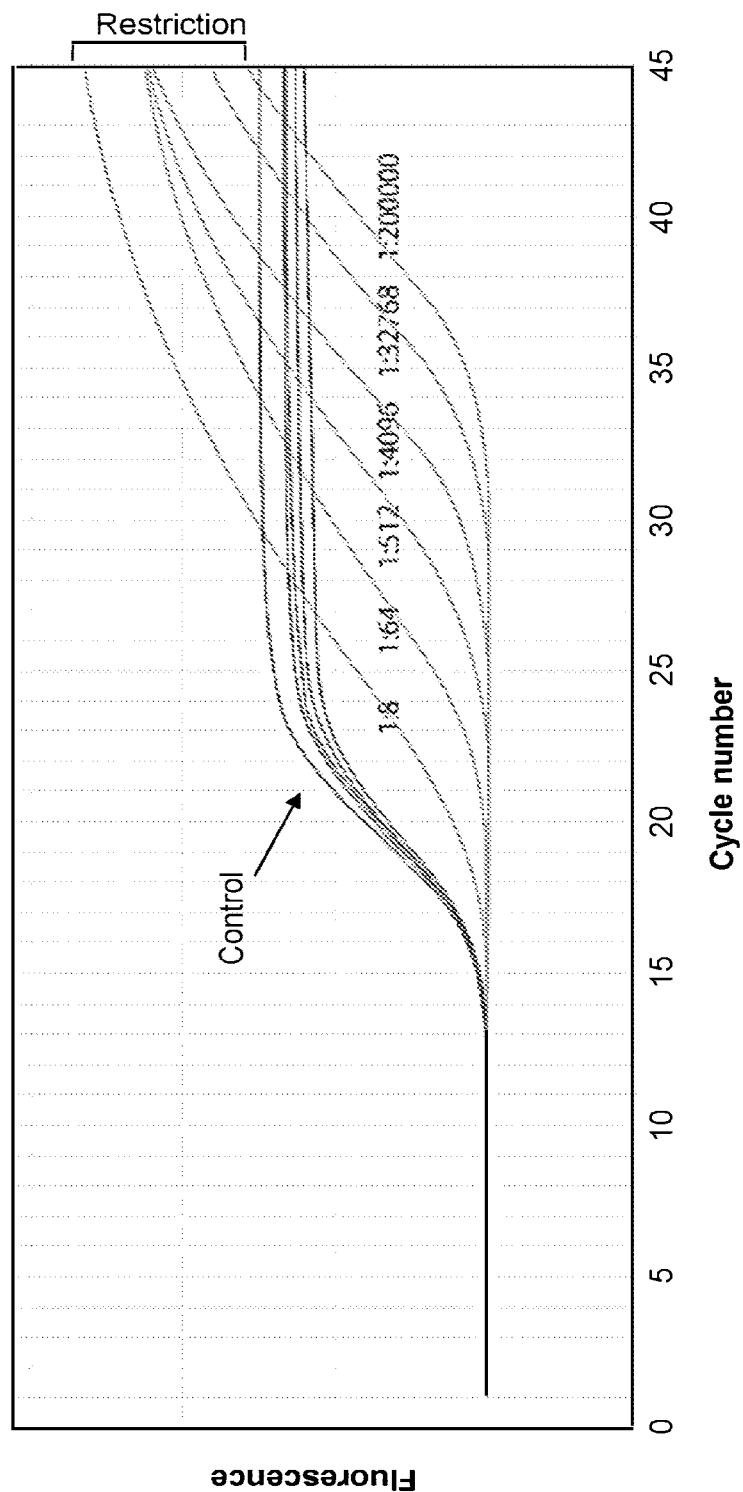
FIG. 2B shows amplification plots of mixtures of methylated and unmethylated DNA. The plots of six separate PCR reactions are superimposed. The internal reference ("Control") is amplified roughly at the same cycle in all reactions, mostly reflecting amplification from the 4,000,000 unmethylated DNA template molecules. With decreasing amounts of methylated DNA, the test locus ("Control") is amplified in increasing ACQs compared to the control locus.
Figure 3:
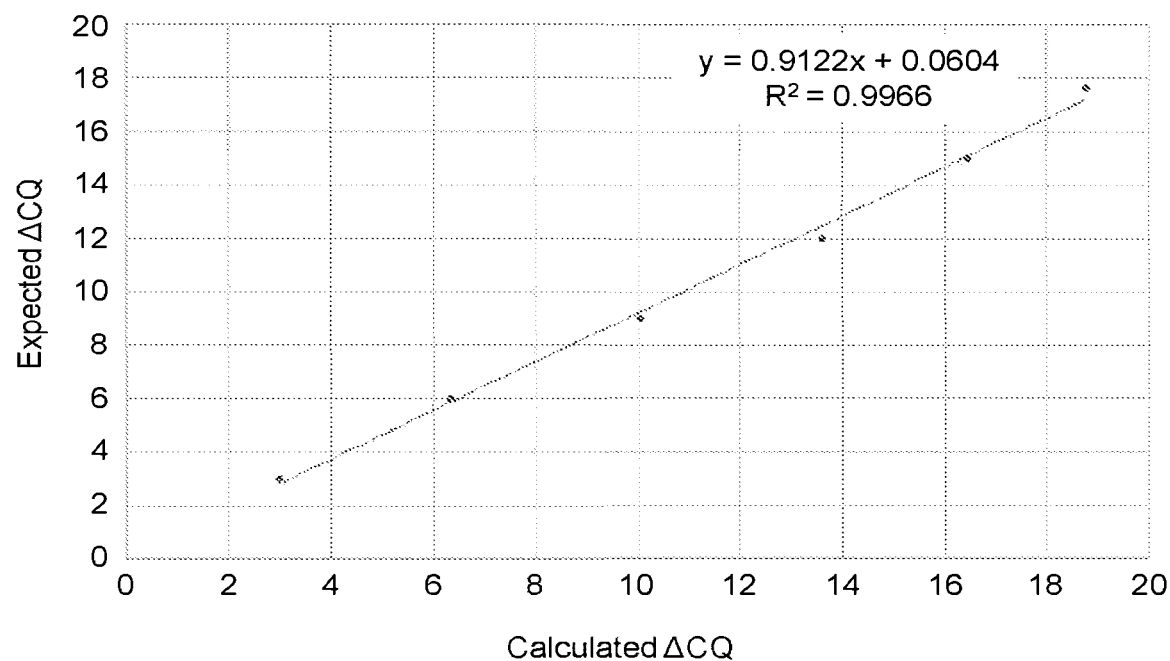
FIG. 3 shows linear regression fit of expected vs. calculated ACQs between the test and internal reference loci.

FIG. 2B shows the amplification plots of the DNA mixtures. For the mixture of DNA with 1:8 molar ratio, the ΔCq between the test and internal reference loci is about 3 cycles. As the ratio between the methylated and unmethylated DNA samples grows, so does the ΔCq, until it reaches 18.75 cycles for the 1:200,000 mix. When the calculated ΔCqs are plotted against the expected ΔCqs (expected ΔCq for methylation level x=−log 2(x)), assuming 100% PCR efficiency for both test and internal reference loci, and linear regression is performed using the least squares method, the resulting fit has an $R^2$ value of 0.9966 (FIG. 3), demonstrating that actual methylation levels can be determined from the ΔCqs.

Figure 4A:
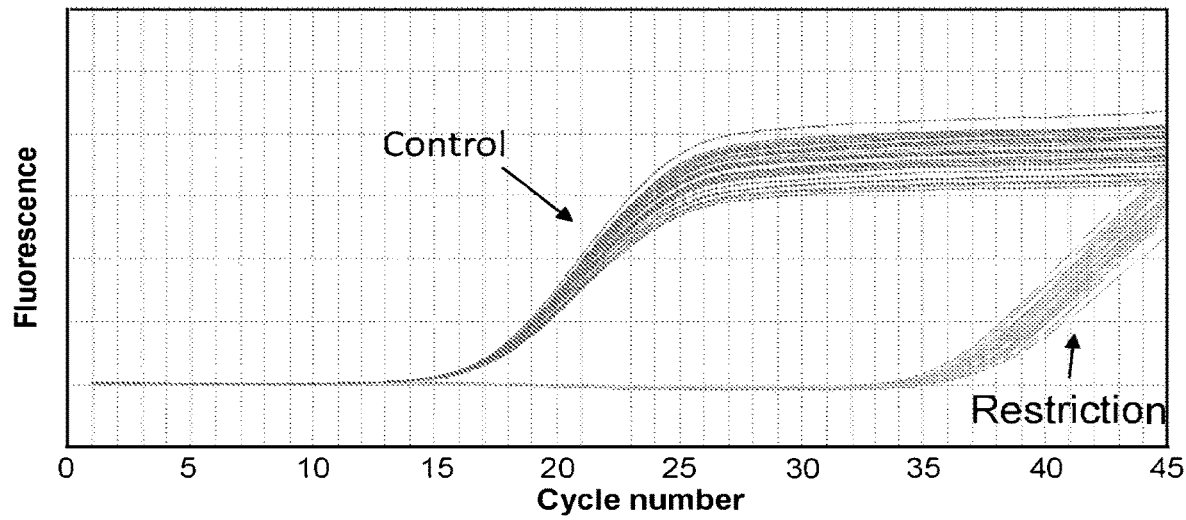
FIGS. 4A and 4B show amplification plots of the 1:200,000 methylated:unmethylated DNA samples (Figure A) and pure unmethylated DNA samples (Figure B). Plots of 34 replicate PCRs are superimposed.
Figure 4B:
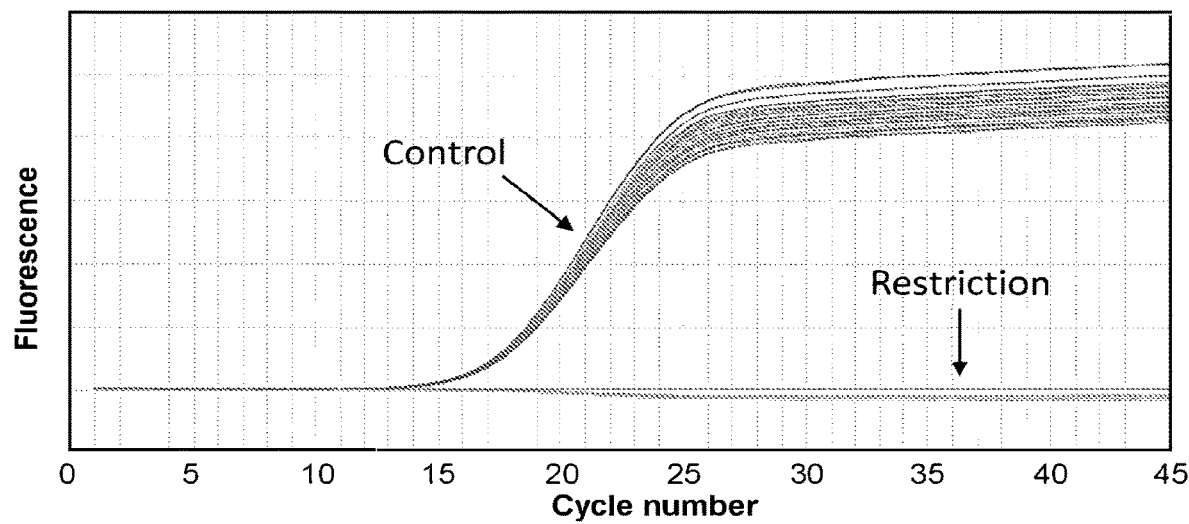

In the next step, in order to demonstrate that the assay can consistently detect methylated molecules with a background of unmethylated molecules at a ratio of 1:200,000, the mixture of DNA samples with this ratio was tested in 34 separate PCR reactions (replicates), in which each well contained 10 methylated (from HCT-15) and 2,000,000 unmethylated (from plasmid DNA) test locus template molecules, and the signal was compared to 34 PCR reactions containing only 2,000,000 unmethylated DNA molecules per well, without any methylated DNA template molecules. FIGS. 4A-B show the amplification plot from this experiment. In all 34 replicates containing the mixture of methylated and unmethylated DNA samples, the test locus was amplified successfully (FIG. 4A), whereas in all 34 replicates containing only unmethylated DNA, no amplification of the test locus was observed (FIG. 4B).

The overall detection rate was 100.0% (68/68). The lower limit of the one-sided exact binomial 95% Confidence Interval (CI) was 95.69%, meaning that the true overall detection rate was higher than 95.69% with 95% confidence. The positive and negative detection rates were both 100.0% (34/34). The lower limit of the one-sided exact binomial 95% CI was 91.57%, meaning that the true positive and negative detection rates were higher than 91.5% with 95% confidence.

This work describes a simple and ultrasensitive assay that can detect methylation levels as low as 1:200,000. Such high sensitivity can be valuable for liquid biopsy samples, in which tumor DNA is usually present in extremely low amounts in relation to the background consisting of normal DNA. The clinical utility of methylation assays with extreme sensitivities is also limited by the amount of input DNA that can be analyzed, the level of background biological noise (i.e. the typical level of methylation obtained from control samples), and the level of biological signal (i.e. the percentage of patients who display the abnormal methylation pattern in their tumor). The amount of input DNA sets an upper limit to the actual sensitivity that can be achieved in an assay. For example, A typical sample of 10 ml venous blood typically yields only ~35 ng of cell free DNA from the 3-4 ml plasma, corresponding to ~10,000 haploid genomic copies. The average number of genomic copies that are analyzed in each well according to the assay of the present invention is ~1,000, setting the highest level of sensitivity that could be achieved with this configuration to ~1:1000, or 0.1%.

Example 4—DNA Extraction and Detection of Methylation Changes at Lung Cancer-Associated Genomic Loci Detection of methylation changes at lung cancer-associated genomic loci in a DNA sample extracted from a plasma sample is carried out as described in Example 1. The extraction of the DNA from the plasma sample is carried out by organic DNA extraction to obtain a DNA sample containing less than 1% ssDNA, as follows:

placing 1 ml plasma in a tube (15 ml or 50 ml tube);
adding to the tube 500 µl extraction buffer (300 mM Tris pH 8.0, 30 mM EDTA, 300 mM NaCl, 6% SDS), 30 µl proteinase K (20 mg/ml) and 150 of 390 nM DTT;
sealing the tube (e.g. with parafilm) and incubating for 2 h at 56° C.;
in a chemical hood, adding 1.5 ml of a mixture of phenol:chloroform:isoamylalcohol (25:24:1) equilibrated overnight to 2-8° C.;
sealing the tube (e.g. with parafilm) and shaking (vortex) for 30 seconds;
separating phases (in a centrifuge, 3 min, 10,000 g);
in a chemical hood, removing the aqueous phase into another tube and adding an equal volume of a mixture of chlorophorm:isoamylalcohol (24:1);
sealing the tube (e.g. with parafilm) and shaking (vortex) for 30 seconds;
separating phases (in a centrifuge, 3 min, 10,000 g);
removing the aqueous phase into another tube and adding a 0.1 volume of 3M NaAc and 2-2.4 volume of ethanol (absolute);
incubating the tube for 20 min at −20° C.;
precipitating the DNA (in a centrifuge, 20 min, 17,000 g, 4° C.);
discarding the ethanol/NaAc solution and washing the remaining sample with ethanol (70%);
pelleting the DNA (in a centrifuge, 15 min, 17,000 g, 4° C.);
discarding the ethanol and drying the pellet; and
resuspending the pellet in ddH$_2$O or a 0.04% NaN$_3$ solution.

Example 5—Next-Generation-Sequencing (NGS)-Based Assay

Materials and Methods

Primer Design for NGS Library Preparation—1$^{st}$ PCR

In order to amplify cancer marker loci for the NGS-based assay, primers were designed which contain the following overhang adapter sequences in addition to the locus-specific sequences:

Forward primer overhang:
(SEQ ID NO: 8)
5' TCGTCGGCAGCGTCAGATGTGTATAAGAGACAG '3

Reverse primer overhang:
(SEQ ID NO: 9)
5' GTCTCGTGGGCTCGGAGATGTGTATAAGAGACAG '3

The overhang adapter sequences were 5' of the locus specific sequence.

In between the overhang adapters and the locus specific sequences either 0, 1, 2 or 3 N nucleotides were added. This addition was done in order to insure even distribution of all four bases in each sequencing cycle. The addition of these N nucleotides was in both forward and revers primers. Overall, there were four forward and four revers primers for each locus.

Four cancer methylation marker loci, a control locus and KRAS exon2 locus were used for this experiment.

The four cancer methylation marker loci were as follows:

TABLE 3

Cancer methylation marker loci

| SEQ ID NO. | Nucleic acid sequence |
|---|---|
| 1 | AGTAGCGCCCACTGAGCGGTTTTTCAGTTGCTGCACCGTTCTT AGCGCCCAACGGAACGTTTCCCGTACGCGGAGTCCATAAGTT |
| 2 | CGGTCCCGCA GCGCCCGCCA CACACCCGCG CCAGAGGTCC AGCGCATGTG CAGTGAAATG GCCTAGCCC |
| 3 | CGGATAGCGC GGCGGGCGAC AGCCCCCCGG ATAACCCCGC CGAGGGAGGG GCGCTTGTAA AACCGAGCGG CG |
| 4 | TCCTCCTTGC CTTCTTTCGC CGAAAGGGGG CGCGCTCCTC CCAGGCTGCG CTGGTACCTA |

These loci contain at least one recognition site of the methylation-sensitive restriction enzyme HhaI.

The control locus was the locus set forth in SEQ ID NO: 7 noted above. This locus does not include a recognition site for HhaI.

The primers for the KRAS locus were as follows:

KRAS f:
(SEQ ID NO: 10)
5'TTAAAACAAGATTTACCTCTATTG'3

KRAS r:
(SEQ ID NO: 11)
5'AAATGACTGAATATAAACTTGTGG'3

Sample Selection and Plasma Preparation 8 healthy control plasma samples and 9 cancer patient plasma samples were used in this experiment.

10 ml blood were drawn from each patient in an EDTA blood tube (Becton Dickinson). Each blood tube was centrifuged in a swinging bucket rotor at 1500×g for 10 minutes at room temperature without brake. The plasma layer was then transferred to a new 15 ml tube and centrifuged again at 1500×g for 10 minutes at room temperature without brake. In order to avoid lymphocytes lysis (that will contaminate the cell free DNA) the centrifugation was carried out up to four hours after the blood collection.

DNA Extraction

DNA extraction from plasma samples was carried out using an extraction kit that produces minimum single strand DNA in the extraction procedure, namely, below 5% ssDNA (QIAamp Circulating Nucleic Acid Kit—Qiagen).

Plasma Separation Test

Before proceeding to digestion, the extracted DNA was tested for contamination with lymphocytes DNA with a plasma separation assay as described in a co-pending application, WO 2019/162941, assigned to the Applicant of the present invention. Such contamination can interfere with the signal of tumor cell free DNA. Only samples that passed the plasma separation assay proceeded to library preparation.

DNA Digestion

The extracted cell-free DNA was subjected to methylation-sensitive digestion for 2 h at 37° C. The reaction was stopped by incubation at 65° C. for 20 min.

Library Preparation for NGS Analysis $1^{st}$ PCR—Locus Specific:

The four cancer methylation marker loci, the control locus and the KRAS locus described above were amplified from the digested DNA samples in two multiplexes (3 loci in each multiplex plus the control locus, which was amplified in each multiplex) using locus specific primers that contain the 5' overhang adapters described above and 0-3 N nucleotides between the locus specific sequences and the 5' overhang adapter sequences. 10 μl of digested DNA were amplified in a 25-cycles PCR reaction using a high-fidelity DNA polymerase.

The digested DNA in the present experiment includes high concentrations of magnesium. Magnesium is also typically present in PCR reaction buffers of high-fidelity DNA polymerases. In order to avoid excess magnesium that might inhibit the PCR reaction, that magnesium concentration in the amplification reaction is adjusted according to the DNA polymerase that is used.

PCR Purification:

After the loci specific PCR, the PCR products were purified using AMPure XP beads (Beckman Coulter Genomics). After purification, the PCR products of the two multiplexes, for each sample, were mixed together $2^{nd}$ PCR—Addition of Illumina Adapters and Sample Indices:

In order to add Illumina adapters and sample indices, a second PCR was performed using primers from Nextera NT index kit (Illumina).

5 μl from the mix of PCR products of the two multiplexes were taken for an 8-cycles PCR reaction that included also 50 from each Nextera primer (N7 and S5) and 25 μl KAPA HiFi HotStart Ready Mix (KAPA Biosystems).

PCR Purification:

After the second PCR, the PCR products were purified using AMPure XP beads (Beckman Coulter Genomics).

Quantification, Dilution and Library Pool Preparation:

The purification products were quantified using Qubit 3.0 fluorometer and dsDNA high sensitivity assay kit (Thermo Fisher Scientific). The PCR purification products were diluted to 1 nM.

5 μl from each diluted purification products were polled together to create polled libraries sample.

NGS Run

The DNA libraries were sequenced on iSeq 100 system (Illumina) using iSeq 100 Reagent kit.

45 pM of polled libraries sample+20% PhiX library (Illumina) was inserted to the iSeq 100 flow cell.

Analysis of Sequence Reads

For each sample the reads files were analyzed using a software as follow:

Target Assignment:

The first 10 letters of each read were searched for an exact match for one of the targets. If such match was found, the target score for the read increased by 1.

The search action was repeated by shifting 5 letters in the read and searching the next 10 letters for an exact match for one of the targets. If such match was found, the target score for the read increased by 1. The process is repeated until the end of the read.

The target with the highest score (with minimum score=2) is the selected target for the read.

Locus Determination:

After locus assignment, the software goes over the read and finds the reads with exact match to the target or up to 1 point mutation or insertion/deletion of up to 3 consecutive nucleotides. These reads will go to up to a "1 mutation" folder. All other reads assigned for this target locus will go to a "more than 1 mutation" folder.

Mutation Analysis:

In this experiment a nucleotide substitution in KRAS locus was defined as "mutation" if more than 1% of the reads in the "up to 1 mutation" file, contained the nucleotide substitution.

Calculation of Relative Copy Number:

Relative copy number was calculated for each locus (from the "up to 1 mutation" folder) in each sample as follows:

Relative copy number=Read number of locus
X/Read number of control locus.

Results

Figure 5:
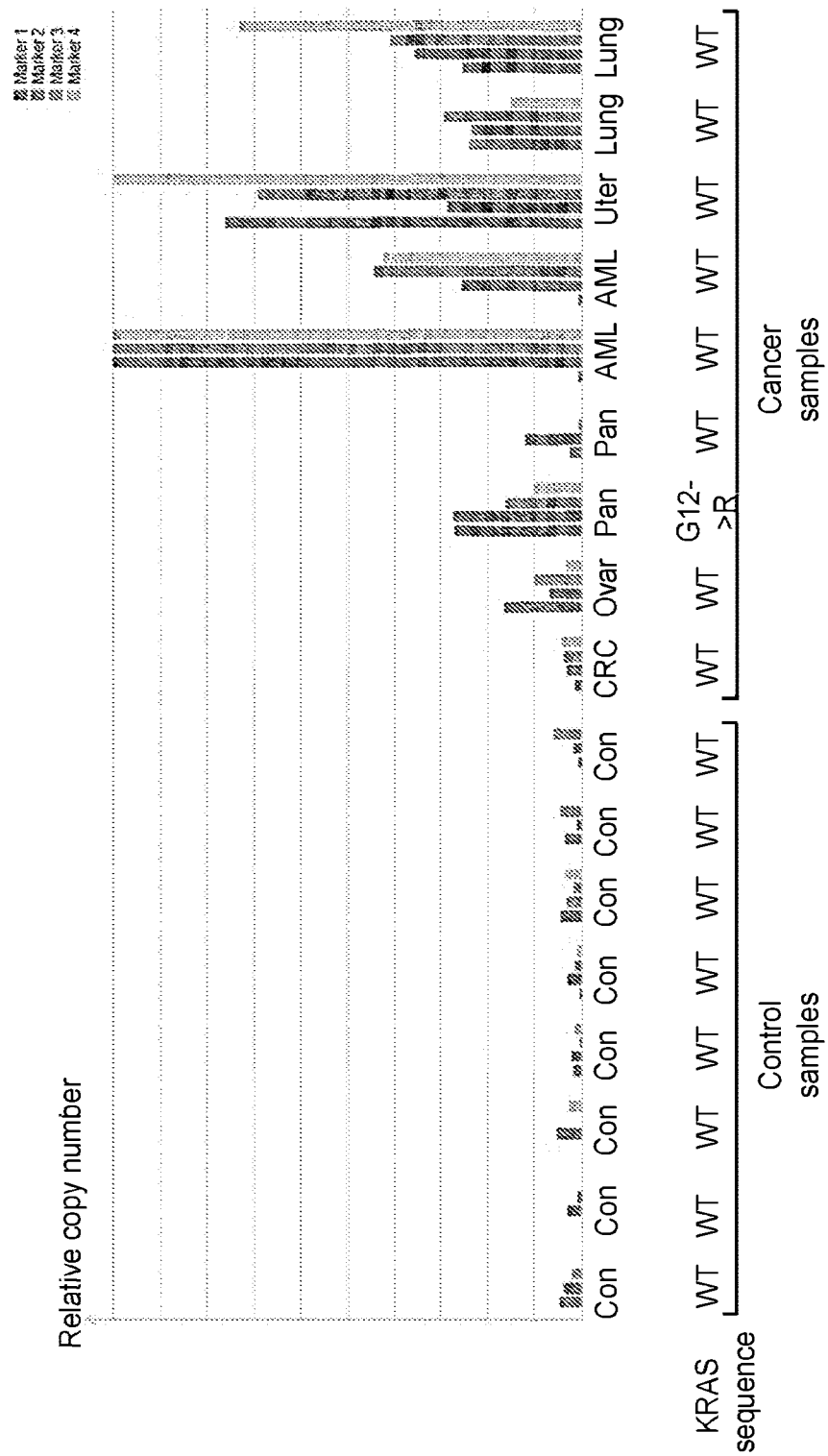
FIG. 5 shows relative copy number of four cancer methylation markers and KRAS mutation status in 8 control samples and 9 cancer samples using an NGS-based assay. Con=control, CRC=colorectal cancer, Ovar=ovarian cancer, Pan=pancreatic cancer, AML=acute myeloid leukemia, Uter=uterine cancer, Lung=lung cancer

NGS-Based Methylation Assay can Differentiate Between Non-Cancer and Cancer Patients 8 healthy control plasma samples and 9 cancer patient plasma samples were analyzed for methylation using four cancer methylation markers, and for KRAS mutations (G12, G13) in the NGS-based assay. The results are summarized in FIG. 5. Methylation level is represented by the relative copy number for each marker (the ratio between the number of reads for each methylation marker in each sample and the number of reads of the control locus in the sample). FIG. 5 shows a significant difference in relative copy numbers of the four markers (corresponding to significant differences in methylation levels) between the control samples and the cancer samples. A mutation in KRAS was detected in one pancreatic cancer sample (G12→R). No KRAS mutations were detected in the control samples.

The results show that an NGS-based assay as described herein can be used for detecting methylation changes indicative of cancer, combined with mutation analysis.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for sensitive detection of methylation changes in a DNA sample, the method comprising:
 (a) providing a DNA sample, wherein the DNA sample contains less than 5% single-stranded DNA (ssDNA); and
 (b) subjecting the DNA sample to methylation ratio analysis by digesting the DNA sample with at least one methylation-sensitive restriction endonuclease or at least one methylation-dependent restriction endonuclease, co-amplifying from the digested DNA at least one restriction locus differentially methylated between normal and disease DNA and at least one control locus in a single reaction mixture, and comparing a ratio between signal intensities of the amplification products of each of said at least one restriction locus and the control locus to at least one reference ratio, thereby detecting methylation changes in the DNA sample at a detection sensitivity of at least 1:100, wherein the DNA is cell-free DNA extracted from a biological fluid sample.

2. The method of claim 1, wherein the DNA in the DNA sample comprises cell-free DNA extracted from a human biological fluid sample and the DNA sample contains less than 5% human ssDNA.

3. The method of claim 2, wherein the biological fluid sample is plasma, serum or urine.

4. The method of claim 1, wherein the DNA sample contains less than 1% human ssDNA.

5. The method of claim 1, wherein the DNA sample contains less than 0.1% human ssDNA.

6. The method of claim 1, wherein the DNA sample contains less than 0.01% human ssDNA or is free of human ssDNA.

7. The method of claim 1, wherein methylation changes are detected in the sample at a detection sensitivity of at least 1:500.

8. The method of claim 1, wherein methylation changes are detected in the sample at a detection sensitivity of at least 1:1,000.

9. The method of claim 1, wherein detecting methylation changes comprises determining whether the DNA sample is a normal or disease DNA sample.

10. The method of claim 9, comprising determining whether the DNA sample is a normal DNA sample or a cancer DNA sample.

11. The method of claim 1, wherein the methylation ratio analysis in step (b) is performed using real-time PCR.

12. The method of claim 1, wherein the methylation ratio analysis in step (b) is performed using Next Generation Sequencing (NGS).

13. The method of claim 1, comprising amplifying in step (b) a plurality of restriction loci differentially methylated between normal and disease DNA and a single control locus.

14. A method for measuring methylation ratio of DNA from a human subject, the method comprising:
(a) providing a DNA sample from the human subject, wherein the DNA sample contains less than 5% human ssDNA; and
(b) subjecting the DNA sample to methylation ratio analysis by digesting the DNA sample with at least one methylation-sensitive restriction endonuclease or at least one methylation-dependent restriction endonuclease, co-amplifying from the digested DNA at least one restriction locus differentially methylated between normal and disease DNA and at least one control locus in a single reaction mixture, and calculating, using software stored in non-transitory memory and implemented on a computer processor, a ratio between the signal intensities of the amplification products of each of said at least one restriction locus and the control locus, thereby measuring methylation ratio of DNA from the human subject, with methylation detection sensitivity of at least 1:100.

15. A system for detecting methylation changes in a DNA sample, the system comprising:

(a) a DNA sample, wherein the DNA sample contains less than 1% ssDNA; and
(b) components for carrying out a methylation ratio analysis, comprising: (i) at least one methylation-sensitive restriction endonuclease or at least one methylation-dependent restriction endonuclease for digesting the DNA sample; (ii) a plurality of primer pairs for co-amplification of a plurality of genomic loci in a single reaction mixture from the DNA sample following digestion, wherein the plurality of genomic loci comprises at least one restriction locus differentially methylated between normal and disease DNA and at least one control locus; and (iii) computer software stored on non-transitory computer readable medium, the computer software directs a computer processor to determine methylation changes in the DNA sample based on a comparison of a ratio of signal intensities of the restriction locus and the control locus following amplification to a reference ratio, with the methylation changes determined at a detection sensitivity of at least 1:100.

16. The system of claim 15, wherein the DNA is cell-free DNA extracted from a human biological fluid sample.

17. The system of claim 16, wherein the biological fluid sample is plasma, serum or urine.

18. The system of claim 16, wherein the DNA sample contains less than 1% human ssDNA.

19. The system of claim 16, wherein the DNA sample contains less than 0.1% human ssDNA.

20. The system of claim 16, wherein the DNA sample contains less than 0.01% human ssDNA or is free of human ssDNA.

21. The system of claim 15, wherein the methylation changes are determined at a detection sensitivity of at least 1:500.

22. The system of claim 15, wherein the methylation changes are determined at a detection sensitivity of at least 1:1,000.

23. The system of claim 15, wherein the plurality of loci comprises a plurality of restriction loci differentially methylated between normal and diseased DNA and a single control locus.

24. The system of claim 15, wherein the methylation changes are determined by performing the following steps: calculating signal intensities for amplification products of the restriction locus and the control locus; calculating a ratio between the signal intensities of the amplification products; and comparing the calculated ratio to one or more reference ratios obtained from DNA samples of known sources.

25. The system of claim 15, wherein determining methylation changes in the DNA sample comprises providing an indication whether the DNA sample is a normal or diseased DNA sample.

26. The system of claim 15, wherein determining methylation changes in the DNA sample comprises providing an indication whether the DNA sample is a normal DNA sample or a cancer DNA sample.

27. The system of claim 15, wherein the components for carrying out a methylation ratio analysis further comprise a plurality of fluorescent probes for detecting the amplification products of the at least one restriction locus and the at least one control locus.

28. The system of claim 15, further comprising DNA extraction reagents to extract DNA from a biological sample, wherein the extracted DNA contains less than 1% ssDNA.

* * * * *